(12) United States Patent
Schmidt et al.

(10) Patent No.: US 9,506,029 B2
(45) Date of Patent: Nov. 29, 2016

(54) RESPONSIVE CELL CULTURE HYDROGEL

(75) Inventors: Daniel Schmidt, Tewksbury, MA (US); Emmanuelle Reynaud, Tewksbury, MA (US); Peter Gaines, Dunstable, MA (US)

(73) Assignee: University of Massachusetts Lowell, Boston, MA (US)

( * ) Notice: Subject to any disclaimer, the term of this patent is extended or adjusted under 35 U.S.C. 154(b) by 203 days.

(21) Appl. No.: 13/976,645

(22) PCT Filed: Dec. 30, 2011

(86) PCT No.: PCT/US2011/068054
§ 371 (c)(1),
(2), (4) Date: Sep. 6, 2013

(87) PCT Pub. No.: WO2012/092542
PCT Pub. Date: Jul. 5, 2012

(65) Prior Publication Data
US 2013/0337566 A1 Dec. 19, 2013

Related U.S. Application Data

(60) Provisional application No. 61/428,383, filed on Dec. 30, 2010.

(51) Int. Cl.
*C12N 5/00* (2006.01)
*C08J 3/075* (2006.01)

(52) U.S. Cl.
CPC .............. *C12N 5/0018* (2013.01); *C08J 3/075* (2013.01); *C12N 5/0068* (2013.01); *C08J 2371/02* (2013.01); *C08J 2379/02* (2013.01); *C08J 2379/04* (2013.01); *C08J 2383/08* (2013.01); *C12N 2533/30* (2013.01)

(58) Field of Classification Search
CPC .............. C12N 5/0018; C12N 5/0068; C12N 2533/30; C08J 3/075; C08J 2379/02; C08J 2379/04; C08J 2383/08; C08J 2371/02
See application file for complete search history.

(56) References Cited

U.S. PATENT DOCUMENTS

| | | | |
|---|---|---|---|
| 4,515,162 A | 5/1985 | Yamamoto et al. | |
| 5,955,549 A | 9/1999 | Chang et al. | |
| 2004/0166579 A1 | 8/2004 | Block | |
| 2006/0222596 A1* | 10/2006 | Askari et al. | 424/9.41 |
| 2009/0190135 A1* | 7/2009 | Clarizia et al. | 356/432 |

FOREIGN PATENT DOCUMENTS

WO WO-2005035735 A2 4/2005

OTHER PUBLICATIONS

Zhao, C., et al.; Journal of Polymer Science, Part A: Polymer Chemistry, 2005, p. 4017-4029.*
Huntsman; Jeffamine® ED-600 Polyetheramine Technical Bulletin, p. 1-2, 2008.*
Stile, Ranee A., et al., "Thermo-Responsive Peptide-Modified Hydrogels for Tissue Regeneration", Biomacromolecules, 2001, vol. 2, No. 1, pp. 185-194.
Chen, Hong, et al., "Ultrafine Hydrogel Fibers with Dual Temperature- and pH-Responsive Swelling Behaviors", Journal of Polymer Science: Part A: Polymer Chemistry, 2004, vol. 42, pp. 6331-6339.
Martin, U., et al., "Advances in Biochemical Engineering/Biotechnology", Engineering of Stem Cells, Springer, 2009, vol. 114, p. 119.
Kavanagh, C. A., et al., "Poly(N-isopropylacrylamide) copolymer films as vehicles for the sustained delivery of proteins to vascular endothelial cells", Journal of Biomedical Materials Research, 2005, 72A, pp. 25-35.
Burdick, Jason A., et al., "Delivery of osteoinductive growth factors from degradable PEG hydrogels influences osteoblast differentiation and mineralization", Journal of Controlled Release, 2002, vol. 83, pp. 53-63.
Kaysinger, Kathleen K., et al., "Extracellular pH Modulates the Activity of Cultured Human Osteoblasts", Journal of Cellular Biochemistry, 1998, vol. 68, pp. 83-89.
Roldan, Jorge E., "Hydrogels: Introduction and Applications in Biology and Engineering", Jun. 25, 2003, pp. 1-22.
Amresco, Inc., "Amresco: The Solution for All of Your Buffer Needs", 2001, pp. 1-10.
Ozturk, Sadettin S., et al., "Chemical Decomposition of Glutamine in Cell Culture Media: Effect of Media Type, pH, and Serum Concentration", Biotechnology Progress, 1990, vol. 6, pp. 121-128.
"Cell Culture Media" accessed online at http://bioxys.com/i_Biochrom/cell_culture_media.htm on Oct. 31, 2011, pp. 1-4; publically available 2005.
Morishita, Mariko, et al., "Elucidation of the mechanism of incorporation of insulin in controlled released systems based on complexation polymers", Journal of Controlled Release, 2002, vol. 81, pp. 25-32.
Peppas, Nicholas A., et al., "Hydrogels in Biology and Medicine: From Molecular Principles to Bionanotechnology", Advanced Materials, 2006, vol. 18, pp. 1345-1360.
Peppas, Nikolaos A., et al., "Preparation, structure and diffusional behavior of hydrogels in controlled release", Advanced Drug Delivery Reviews, 1993, vol. 11, pp. 1-35.
Qui, Yong, et al., "Environment-sensitive hydrogels for drug delivery", Advanced Drug Delivery Reviews, 2001, vol. 53, pp. 321-339.
Hennink, W. E., et al., "Novel crosslinking methods to design hydrogels", Advanced Drug Delivery Reviews, 2002, vol. 54, pp. 13-36.
Park, Jae Hyung, et al., "Hydrogels based on poly(ethylene oxide) and poly(tetramethylene oxide) or poly(dimethyl siloxane): synthesis, characterization, in vitro protein adsorption and platelet adhesion", Biomaterials, 2002, vol. 23, pp. 1797-1808.
Shechter, Emanuel, et al., "Fluorescence Dye As Monitor of Internal pH in *Escherichia Coli* Cells", Federation of European Biochemical Societies, Mar. 1982, vol. 139, No. 1, pp. 121-124.

(Continued)

*Primary Examiner* — Robert Jones, Jr.
(74) *Attorney, Agent, or Firm* — McCarter & English, LLP; Danielle L. Herritt, Esq.; Patrick A. Walker, III

(57) ABSTRACT

The present invention provides devices, compositions and methods for maintaining conditions in a cell culture and for measurement of conditions in the cell culture. In particular, the invention provides hydrogel materials, apparatus and methods for several non-invasive techniques of maintaining optimal or near-optimal nutrient and pH levels in cell cultures.

22 Claims, 18 Drawing Sheets

(56) References Cited

OTHER PUBLICATIONS

Satish, C., et al., "Hydrogels as controlled drug delivery systems: Synthesis, crosslinking, water and drug transport mechanism", Indian Journal of Pharmaceutical Sciences, Mar.-Apr. 2006, pp. 1-10.
Park, Jae Hyung, et al., "Hydrogels Based on Poly(ethylene oxide) and Poly(tetramethyleneoxide) or Poly(dimethyl siloxane). II. Physical Properties and Bacterial Adhesion", Journal of Applied Polymer Sciences, 2003, vol. 89, pp. 1505-1514.
Kim, Seon Jeong, et al., "Synthesis and Characteristics of Semi-interpenetrating Polymer Network Hydrogels Based on Chitosan and Poly(hydroxy ethyl methacrylate)", Journal of Applied Polymer Sciences, 2005, vol. 96, pp. 86-92.
Czajkowska, Barbara, et al., "Interaction of cells with L-lactide/glycolide copolymers synthesized with the use of tin or zirconium compounds", Journal of Biomedical Materials Research, 2005, vol. 74A, pp. 591-597.
Tanzi, M. C., et al., "Cytotoxicity of some catalysts commonly used in the synthesis of copolymers for biomedical use", Chapman & Hall, 1994, pp. 393-396.
Kricheldorf, Hans R., et al., "Bismuth(III) n-Hexanoate and Tin(II) 2-Ethylhexanoate Initiated Copolymerizations of $\epsilon$-Caprolactone and L-Lactide", Macromolecules, 2005, vol. 38, No. 12, pp. 5017-5024.
Steinlein, Christian, et al., "Synthesis and thermal stability of oligourethanes based on the cycloaliphatic diisocyanate trans, trans-4,4'-methylenebis(cyclohexylisocyanate)", Macromolecular Chemistry and Physics, 1996, vol. 197, pp. 3365-3382.
Lin, Jiang-Jen, et al., "Thermal stability of poly(oxyalkylene)amine-grafted polypropylene copolymers", Polymer Degradation and Stability, 2000, vol. 70, pp. 171-184.
Chuang, F.S., et al., "The effect of different siloxane chain-extenders on the thermal degradation and stability of segmented polyurethanes", Polymer Degradation and Stability, 2004, vol. 84, pp. 69-77.
Podual, Kairali, et al., "Relaxational behavior and swelling-pH master curves of poly[(diethylaminoethyl methacrylate)-graft-(ethylene glycol)] hydrogels", Polymer International, 2005, vol. 54, pp. 581-593.
Aguilar, M.R. et al., "Smart Polymers and Their Applications as Biomaterials", Topics in Tissue Engineering, 3:1-27, 2007.

\* cited by examiner

Change in pH over 24 hours due to hydrogel in DMEM medium with added lactic acid

Changes in glucose released from loaded hydrogel in regular medium vs. medium plus lactic acid

Figure 10
Table 1

| NANI | Components | | | f (meq/g) | | | Mass fraction | | | Groups (mmol/mL) | | | |
|---|---|---|---|---|---|---|---|---|---|---|---|---|---|
| | A | B | C | A | B | C | A | B | C | A | B | C | Total |
| H-600 | Jeffamine ED-600 | - | Heloxy 48 | 7.58 | - | 7.04 | 0.482 | - | 0.518 | 3.650 | - | 3.650 | 7.299 |
| H-900 | Jeffamine ED-900 | - | Heloxy 48 | 4.00 | - | 7.04 | 0.638 | - | 0.362 | 2.551 | - | 2.551 | 5.102 |
| H-2003* | Jeffamine ED-2003 | - | Heloxy 48 | 1.74 | - | 7.04 | 0.802 | - | 0.198 | 1.395 | - | 1.395 | 2.789 |
| H-148 | Jeffamine EDR-148 | - | Heloxy 48 | 27.03 | - | 7.04 | 0.207 | - | 0.793 | 5.587 | - | 5.587 | 11.173 |
| H-176 | Jeffamine EDR-176 | - | Heloxy 48 | 22.73 | - | 7.04 | 0.237 | - | 0.763 | 5.376 | - | 5.376 | 10.753 |
| H-BAPP | Bis(3-aminopropyl)piperazine | - | Heloxy 48 | 19.97 | - | 7.04 | 0.261 | - | 0.739 | 5.206 | - | 5.206 | 10.412 |
| H-HP** | Homopiperazine | - | Heloxy 48 | 19.97 | - | 7.04 | 0.261 | - | 0.739 | 5.206 | - | 5.206 | 10.412 |
| H-AEP** | 1-(2-Aminoethyl)piperazine | - | Heloxy 48 | 23.22 | - | 7.04 | 0.233 | - | 0.767 | 5.403 | - | 2.403 | 10.807 |
| H-900/176 | Jeffamine ED-900 | Jeffamine EDR-176 | Heloxy 48 | 4.00 | 22.73 | 7.04 | 0.173 | 0.173 | 0.655 | 0.690 | 3.922 | 4.612 | 9.224 |
| PEG-BAPP* | Bis(3-aminopropyl)piperazine | - | PEG-DGE | 19.97 | - | 1.67 | 0.077 | - | 0.923 | 1.538 | - | 1.538 | 3.077 |
| G-148 | Jeffamine EDR-148 | - | Erisys GE-36 | 27.03 | - | 1.49 | 0.052 | - | 0.948 | 1.414 | - | 1.414 | 2.829 |
| G-176 | Jeffamine EDR-176 | - | Erisys GE-36 | 22.73 | - | 1.49 | 0.062 | - | 0.938 | 1.401 | - | 1.401 | 2.801 |
| G-BAPP | Bis(3-aminopropyl)piperazine | - | Erisys GE-36 | 19.97 | - | 1.49 | 0.070 | - | 0.930 | 1.389 | - | 1.389 | 2.777 |
| G-HP | Homopiperazine | - | Erisys GE-36 | 19.97 | - | 1.49 | 0.070 | - | 0.930 | 1.389 | - | 1.389 | 2.777 |
| G-AEP | 1-(2-Aminoethyl)piperazine | - | Erisys GE-36 | 23.22 | - | 1.49 | 0.060 | - | 0.940 | 1.402 | - | 1.402 | 2.805 |
| G-P600 | Poly(ethyleneimine), MW~600 | - | Erisys GE-36 | 18.90 | - | 1.49 | 0.073 | - | 0.927 | 1.383 | - | 1.383 | 2.767 |
| G-P1200 | Poly(ethyleneimine), MW~1200 | - | Erisys GE-36 | 18.90 | - | 1.49 | 0.073 | - | 0.927 | 1.383 | - | 1.383 | 2.767 |
| G-P1800 | Poly(ethyleneimine), MW~1800 | - | Erisys GE-36 | 18.90 | - | 1.49 | 0.073 | - | 0.927 | 1.383 | - | 1.383 | 2.767 |
| G60-2000* | Jeffamine ED-2003 | - | Erisys GE-60 | 1.74 | - | 5.65 | 0.765 | - | 0.235 | 1.330 | - | 1.330 | 2.660 |
| G60-T3000 | Jeffamine T-3000 | - | Erisys GE-60 | 1.89 | - | 5.65 | 0.750 | - | 0.250 | 1.414 | - | 1.414 | 2.829 |
| G60-T5000 | Jeffamine T-5000 | - | Erisys GE-60 | 1.05 | - | 5.65 | 0.843 | - | 0.157 | 0.886 | - | 0.886 | 1.771 |
| G60-X542 | Jeffamine XTJ-542 | - | Erisys GE-60 | 3.85 | - | 5.65 | 0.595 | - | 0.405 | 2.288 | - | 2.288 | 4.577 |
| G60-X559 | Jeffamine XTJ-559 | - | Erisys GE-60 | 2.82 | - | 5.65 | 0.667 | - | 0.333 | 1.880 | - | 1.880 | 3.759 |
| GGE-600** | Jeffamine ED-600 | - | Glycidyl Glycerol-Ether | 7.58 | - | 6.90 | 0.477 | - | 0.523 | 3.610 | - | 3.610 | 7.220 |
| GGE-900** | Jeffamine ED-900 | - | Glycidyl Glycerol-Ether | 4.00 | - | 6.90 | 0.633 | - | 0.367 | 2.532 | - | 2.532 | 5.063 |
| GGE-2003** | Jeffamine ED-2003 | - | Glycidyl Glycerol-Ether | 1.74 | - | 6.90 | 0.799 | - | 0.201 | 1.389 | - | 1.389 | 2.778 |

Figure 10 (cont'd)
Table 1 (cont'd)

| | | | | | | | | | |
|---|---|---|---|---|---|---|---|---|---|
| GGE-148** | Jeffamine EDR-148 | - | Glycidyl Glycerol-Ether | 27.03 | - | 6.90 | 0.203 | - | 0.797 | 5.495 | - | 5.495 | 10.989 |
| GGE-176** | Jeffamine EDR-176 | - | Glycidyl Glycerol-Ether | 22.73 | - | 6.90 | 0.233 | - | 0.767 | 5.291 | - | 5.291 | 10.582 |
| GGE-BAPP** | Bis(3-aminopropyl)piperazine | - | Glycidyl Glycerol-Ether | 19.97 | - | 6.90 | 0.257 | - | 0.743 | 5.126 | - | 5.126 | 10.252 |
| GGE-HP** | Homopiperazine | - | Glycidyl Glycerol-Ether | 19.97 | - | 6.90 | 0.257 | - | 0.743 | 5.126 | - | 5.126 | 10.252 |
| GGE-AEP** | 1-(2-Aminoethyl)piperazine | - | Glycidyl Glycerol-Ether | 23.22 | - | 6.90 | 0.229 | - | 0.771 | 5.317 | - | 5.317 | 10.635 |
| GGE-900/176** | Jeffamine ED-900 | Jeffamine EDR-176 | Glycidyl Glycerol-Ether | 4.00 | 22.73 | 6.90 | 0.170 | 0.170 | 0.660 | 0.681 | 3.868 | 4.549 | 9.098 |
| | | | | | | | | MIN | 0.018 | 0.313 | 0.331 | 0.661 |
| | | | | | | | | MAX | 5.587 | 3.922 | 5.587 | 11.173 |

Figure 11
Table 2

| NANI | Components | | | Swelling (w/w) | | | | Acid Absorption Capacity | |
|---|---|---|---|---|---|---|---|---|---|
| | A | B | C | pH 2 | pH 9 | Δ | Ratio | (meq / g dry NANI) | (meq / g wet NANI) |
| H-600 | Jeffamine ED-600 | - | Heloxy 48 | 139% | 49% | 90% | 2.8 | 1.55 | 1.04 |
| H-900 | Jeffamine ED-900 | - | Heloxy 48 | 194% | 110% | 84% | 1.8 | 1.38 | 0.66 |
| H-2003 | Jeffamine ED-2003 | - | Heloxy 48 | 660% | 416% | 244% | 1.6 | 0.79 | 0.15 |
| H-148 | Jeffamine EDR-148 | - | Heloxy 48 | 22% | 15% | 7% | 1.5 | 2.63 | 2.29 |
| H-176 | Jeffamine EDR-176 | - | Heloxy 48 | 22% | 13% | 9% | 1.7 | 2.60 | 2.31 |
| H-BAPP | Bis(3-aminopropyl)piperazine | - | Heloxy 48 | 37% | 31% | 6% | 1.2 | 5.21 | 3.96 |
| H-HP | Homopiperazine | - | Heloxy 48 | - | - | - | - | 5.21 | - |
| H-AEP | 1-(2-Aminoethyl)piperazine | - | Heloxy 48 | - | - | - | - | 5.40 | - |
| H-900/176 | Jeffamine ED-900 | Jeffamine EDR-176 | Heloxy 48 | 62% | 28% | 34% | 2.2 | 2.27 | 1.77 |
| PEG-BAPP | Bis(3-aminopropyl)piperazine | - | PEG-DGE | 734% | 479% | 256% | 1.5 | 0.77 | 0.13 |
| G-148 | Jeffamine EDR-148 | - | Erisys GE-36 | 143% | 11% | 133% | 13.6 | 0.66 | 0.60 |
| G-176 | Jeffamine EDR-176 | - | Erisys GE-36 | [200%] | 10% | 190% | 20.8 | 0.68 | 0.62 |
| G-BAPP | Bis(3-aminopropyl)piperazine | - | Erisys GE-36 | 131% | 23% | 107% | 5.6 | 0.69 | 0.56 |
| G-HP | Homopiperazine | - | Erisys GE-36 | [650%] | 33% | 617% | 19.5 | 1.39 | |
| G-AEP | 1-(2-Aminoethyl)piperazine | - | Erisys GE-36 | 145% | 22% | 123% | 6.7 | 1.40 | |
| G-P600 | Poly(ethyleneimine), MW~600 | - | Erisys GE-36 | 44% | 21% | 23% | 2.1 | 1.46 | 1.21 |
| G-P1200 | Poly(ethyleneimine), MW~1200 | - | Erisys GE-36 | 20% | 16% | 5% | 1.3 | 1.39 | 1.20 |
| G-P1800 | Poly(ethyleneimine), MW~1800 | - | Erisys GE-36 | 35% | 22% | 13% | 1.6 | 1.39 | 1.14 |
| G60-2000 | Jeffamine ED-2003 | - | Erisys GE-60 | 483% | 398% | 85% | 1.2 | 0.75 | 0.15 |
| G60-T3000 | Jeffamine T-3000 | - | Erisys GE-60 | 9% | 6% | 3% | 1.5 | 0.70 | 0.66 |
| G60-T5000 | Jeffamine T-5000 | - | Erisys GE-60 | 15% | 8% | 7% | 1.9 | 0.44 | 0.41 |
| G60-X542 | Jeffamine XTJ-542 | - | Erisys GE-60 | 11% | 6% | 6% | 2.1 | 1.17 | 1.11 |
| G60-X559 | Jeffamine XTJ-559 | - | Erisys GE-60 | 10% | 7% | 2% | 1.3 | 0.94 | 0.87 |

Figure 11 (cont'd)
Table 2 (cont'd)

| | | | | |
|---|---|---|---|---|
| GGE-600 | Jeffamine ED-600 | - | Glycidyl Glycerol-Ether | 1.53 |
| GGE-900 | Jeffamine ED-900 | - | Glycidyl Glycerol-Ether | 1.37 |
| GGE-2003 | Jeffamine ED-2003 | - | Glycidyl Glycerol-Ether | 0.78 |
| GGE-148 | Jeffamine EDR-148 | - | Glycidyl Glycerol-Ether | 2.58 |
| GGE-176 | Jeffamine EDR-176 | - | Glycidyl Glycerol-Ether | 2.56 |
| GGE-BAPP | Bis(3-aminopropyl)piperazine | - | Glycidyl Glycerol-Ether | 5.13 |
| GGE-HP | Homopiperazine | - | Glycidyl Glycerol-Ether | 5.13 |
| GGE-AEP | 1-(2-Aminoethyl)piperazine | - | Glycidyl Glycerol-Ether | 5.32 |
| GGE-900/176 | Jeffamine ED-900 | Jeffamine EDR-176 | Glycidyl Glycerol-Ether | 2.24 |
| | | | MIN | 2% | 1.19 | 0.44 |
| | | | MAX | 256% | 20.84 | 2.63 |
| | | | | | | 0.13 |
| | | | | | | 2.31 |

Figure 12
Table 3

| NANI | Components | | | Minimum Glucose Capacity | | Maximum Glucose Capacity | |
|---|---|---|---|---|---|---|---|
| | A | B | C | (mg/g dry NANI) | (mg/g wet NANI) | (mg/g dry NANI) | (mg/g wet NANI) |
| H-600 | Jeffamine ED-600 | - | Heloxy 48 | 197 | 132 | 556 | 233 |
| H-900 | Jeffamine ED-900 | - | Heloxy 48 | 439 | 209 | 775 | 264 |
| H-2003 | Jeffamine ED-2003 | - | Heloxy 48 | 1666 | 323 | 2641 | 347 |
| H-148 | Jeffamine EDR-148 | - | Heloxy 48 | 59 | 51 | 88 | 72 |
| H-176 | Jeffamine EDR-176 | - | Heloxy 48 | 50 | 45 | 87 | 72 |
| H-BAPP | Bis(3-aminopropyl)piperazine | - | Heloxy 48 | 126 | 96 | 150 | 109 |
| H-HP | Homopiperazine | - | Heloxy 48 | - | - | - | - |
| H-AEP | 1-(2-Aminoethyl)piperazine | - | Heloxy 48 | - | - | - | - |
| H-900/176 | Jeffamine ED-900 | Jeffamine EDR-176 | Heloxy 48 | 114 | 89 | 248 | 153 |
| PEG-BAPP | Bis(3-aminopropyl)piperazine | - | PEG-DGE | 1914 | 331 | 2938 | 352 |
| G-148 | Jeffamine EDR-148 | - | Erisys GE-36 | 42 | 38 | 573 | 235 |
| G-176 | Jeffamine EDR-176 | - | Erisys GE-36 | 38 | 35 | 800 | 267 |
| G-BAPP | Bis(3-aminopropyl)piperazine | - | Erisys GE-36 | 93 | 76 | 523 | 227 |
| G-HP | Homopiperazine | - | Erisys GE-36 | 134 | 100 | 2600 | 347 |
| G-AEP | 1-(2-Aminoethyl)piperazine | - | Erisys GE-36 | 87 | 71 | 580 | 237 |
| G-P600 | Poly(ethyleneimine), MW~600 | - | Erisys GE-36 | 85 | 70 | 175 | 122 |
| G-P1200 | Poly(ethyleneimine), MW~1200 | - | Erisys GE-36 | 63 | 54 | 81 | 68 |
| G-P1800 | Poly(ethyleneimine), MW~1800 | - | Erisys GE-36 | 88 | 72 | 142 | 105 |
| G60-2000 | Jeffamine ED-2003 | - | Erisys GE-60 | 1590 | 320 | 1930 | 331 |
| G60-T3000 | Jeffamine T-3000 | - | Erisys GE-60 | 25 | 23 | 36 | 33 |
| G60-T5000 | Jeffamine T-5000 | - | Erisys GE-60 | 32 | 29 | 61 | 53 |
| G60-X542 | Jeffamine XTJ-542 | - | Erisys GE-60 | 22 | 21 | 46 | 41 |

Figure 12 (cont'd)
Table 3 (cont'd)

|  |  |  | 30 | 28 | 39 | 36 |
|---|---|---|---|---|---|---|
| G60-X559 | Jeffamine XTJ-559 | - |  |  |  |  |
| GGE-600 | Jeffamine ED-600 | Glycidyl Glycerol-Ether |  |  |  |  |
| GGE-900 | Jeffamine ED-900 | Glycidyl Glycerol-Ether |  |  |  |  |
| GGE-2003 | Jeffamine ED-2003 | Glycidyl Glycerol-Ether |  |  |  |  |
| GGE-148 | Jeffamine EDR-148 | Glycidyl Glycerol-Ether |  |  |  |  |
| GGE-176 | Jeffamine EDR-176 | Glycidyl Glycerol-Ether |  |  |  |  |
| GGE-BAPP | Bis(3-aminopropyl)piperazine | Glycidyl Glycerol-Ether |  |  |  |  |
| GGE-HP | Homopiperazine | Glycidyl Glycerol-Ether |  |  |  |  |
| GGE-AEP | 1-(2-Aminoethyl)piperazine | Glycidyl Glycerol-Ether |  |  |  |  |
| GGE-900/176 | Jeffamine ED-900 | Jeffamine EDR-176 Glycidyl Glycerol-Ether |  |  |  |  |
|  |  | MIN | 22.10 | 20.94 | 36.40 | 33.36 |
|  |  | MAX | 1914.36 | 330.87 | 2937.72 | 352.06 |

Figure 13

Table 4 pH and Glucose responses of Hydrogels in DMEM medium

| Measurement | pH | Glucose | | |
|---|---|---|---|---|
| | Δ 24 Hr | Slope Normal Medium (8 hrs) | Slope with Lactic Acid (8 hrs) | Δ24 – Normal Medium | Δ24 – Medium with Lactic Acid |
| H-600 | ***0.42 ± 0.03 | 6.81 | 16.58 | 46.0 | 135.3 |
| H-900 | 0.73 ± 0.1 | 12.4 | 17.5 | 119.8 | 270.2 |
| H-148 | 1.56 ± 0.2 | 1.0 | 3.7 | 32 | 64 |
| H-176 | ***1.67 ± 0.1 | 1.7 | 11.1 | 74.7 | 144.0 |
| H-BAPP | 1.3 ± 0.03 | 7.3 | -0.7 | 88 | 64 |
| H900/176 | 0.76 ± 0.02 | 0.7 | 5.3 | 17.3 | 46.7 |
| G-148 | 0.58 ± 0.07 | 2.2 | 5.3 | 25.3 | 48 |
| G-176 | 0.69 ± 0.04 | 0 | 4 | 10.7 | 42.7 |
| G-BAPP | 0.70 ± 0.08 | 2.7 | 3 | 32 | 50.7 |
| G-P600 | 0.723 ± 0.11 | 2 | 4.7 | 36 | 49 |

Figure 14

Table 5

| Composition | Δ·Glucose Capacity | | | | Ratio·Glucose Capacity | | | |
|---|---|---|---|---|---|---|---|---|
| | (min, dry) | (min, hydrogel) | (max, dry) | (max, hydrogel) | (min, dry) | (min, hydrogel) | (max, dry) | (max, hydrogel) |
| H-600 | 177 | 118 | 498 | 209 | 556 | 372 | 1567 | 656 |
| H-900 | 368 | 175 | 649 | 221 | 775 | 369 | 1366 | 465 |
| H-148 | 4 | 4 | 6 | 5 | 88 | 76 | 131 | 107 |
| H-176 | 5 | 4 | 8 | 7 | 87 | 78 | 152 | 125 |
| H-BAPP | 8 | 6 | 9 | 7 | 150 | 114 | 179 | 130 |
| H-900/176 | 38 | 30 | 83 | 51 | 248 | 193 | 541 | 334 |
| G-148 | 56 | 51 | 759 | 312 | 573 | 518 | 7789 | 3203 |
| G-176 | 73 | 67 | 1523 | 508 | 800 | 730 | 16672 | 5557 |
| G-BAPP | 100 | 81 | 561 | 243 | 523 | 424 | 2926 | 1268 |
| G-P600 | 19 | 16 | 40 | 28 | 175 | 145 | 363 | 252 |

Figure 15

Table 6

| Composition | Δ(pH Change) (24 hr) | SD | Glucose Release Rate (8 hr) -LA | Glucose Release Rate (8 hr) +LA | Glucose Increase (24 hr) -LA | Glucose Increase (24 hr) +LA | Δ(Glucose) Release Rate | Δ(Glucose) Increase | Ratio(Glucose) Release Rate | Ratio(Glucose) Increase |
|---|---|---|---|---|---|---|---|---|---|---|
| H-600 | 0.42 | 0.03 | 6.81 | 16.58 | 46 | 135.3 | 9.77 | 89.3 | 2.4 | 2.9 |
| H-900 | 0.73 | 0.1 | 12.4 | 17.5 | 119.8 | 270.2 | 5.1 | 150.4 | 1.4 | 2.3 |
| H-148 | 1.56 | 0.2 | 1 | 3.7 | 32 | 64 | 2.7 | 32 | 3.7 | 2.0 |
| H-176 | 1.67 | 0.1 | 1.7 | 11.1 | 74.7 | 144 | 9.4 | 69.3 | 6.5 | 1.9 |
| H-BAPP | 1.3 | 0.03 | 7.3 | -0.7 | 88 | 64 | -8 | -24 | -0.1 | 0.7 |
| H-900/176 | 0.76 | 0.02 | 0.7 | 5.3 | 17.3 | 46.7 | 4.6 | 29.4 | 7.6 | 2.7 |
| G-148 | 0.58 | 0.07 | 2.2 | 5.3 | 25.3 | 48 | 3.1 | 22.7 | 2.4 | 1.9 |
| G-176 | 0.69 | 0.04 | 0 | 4 | 10.7 | 42.7 | 4 | 32 | 0.0 | 4.0 |
| G-BAPP | 0.7 | 0.08 | 2.7 | 3 | 32 | 50.7 | 0.3 | 18.7 | 1.1 | 1.6 |
| G-P600 | 0.723 | 0.11 | 2 | 4.7 | 36 | 49 | 2.7 | 13 | 2.4 | 1.4 |

RESPONSIVE CELL CULTURE HYDROGEL

RELATED APPLICATIONS

This application is a 35 U.S.C. §371 national stage filing of International Application No. PCT/US2011/068054, filed Dec. 30, 2011, which claims priority to U.S. Provisional Application No. 61/428,383, filed on Dec. 30, 2010, the entire contents of which are incorporated herein by this reference.

BACKGROUND OF THE INVENTION

In vitro cell culturing is a common scientific technique. Successful cell culturing involves, in part, properly preparing and continually monitoring for proper temperature, pH, gas and nutrient content. The present disclosure relates to a novel and responsive cell culture hydrogel.

SUMMARY OF THE INVENTION

An automated, real-time, non-invasive cell-feeding device based on hydrogel technology has been developed. Hydrogels described in the present disclosure are based on synthetic polymers and are useful materials for biological applications because of their high water content and biocompatibility. In preferred embodiments, a pH-sensitive hydrogel will release desired nutrients and/or absorb or scavenge components from the cell culture, for example, small molecules and ions, in response to a decrease in pH of the cell culture. In some embodiments, the hydrogels of the present disclosure absorb or scavenge acidic species (e.g., acidic metabolites; carbon dioxide, for example carbon dioxide from the air or atmosphere; pH buffer species; and the like). In other embodiments, the hydrogels absorb or scavenge species (e.g., uncharged metabolites). In additional embodiments, the incorporation of a pH-sensitive dye allows for qualitative (e.g., based on visual determination of a color change) as well as quantitative (e.g., computed using a sensing device) monitoring of the pH, in conjunction with a method for providing remote broadcasting of information on the health of the cell culture conditions. Various features described in the present disclosure help to eliminate the need for direct human intervention and reduce the chances of contamination.

Embodiments described in the present disclosure offer benefits and improvements over current cell culturing methods. Hydrogels can consist of inexpensive, commercially available components (materials costing only a few dollars per pound) and may be produced easily and rapidly. Embodiments of the present disclosure also reduce the chances of contamination as well as cell distress or death from nutrient depletion or suboptimal conditions. Companies can reduce the time and money spent on overtime, while staff will be able to enjoy their time off without worrying about their cell cultures on weekends and holidays. More importantly, maintenance of optimal conditions may extend the viability of cells in small volumes (e.g., those provided by 96-well-plates) often used in large drug screening protocols, or prevent changes in cell characteristics, a particular concern for cells prone to differentiation, including embryonic stem cells. By optimizing the growth of cells and reducing cell death due to suboptimal conditions, embodiments of the present disclosure serve as an enabling technology that may allow scientists to accelerate their studies and companies to move products faster to market, and provide for more reliable results from their studies.

In one aspect of the present disclosure, a method for delivering one or more agents to a cell is provided, wherein a hydrogel with one or more agents is provided to a cell and the cell is cultured under conditions such that the one or more agents is released into the media and delivered to the cell. In another aspect of the present disclosure, the hydrogel is responsive to changes in the pH of the media.

The present disclosure also provides a method for maintaining an optimal cell culture pH by providing a pH-sensitive hydrogel of the present disclosure with a pH-regulating agent and/or buffer. In certain embodiments, the agent and/or buffer, the hydrogel itself or combinations thereof maintains the cell culture pH. They hydrogel may comprise pH active groups. An additional aspect of the method maintains cell culture within an optimal range of 6 to 8.5 (e.g., between 6.2 and 8.2, between 6.5 and 8.0, or between 6.8 and 7.4) pH units. One or more nutrients are included in the hydrogel of the present disclosure in a further aspect, such as, for example, glucose, amino acids, growth factors and L-glutamine. Since L-glutamine may not be stable for long periods of time in a cell culture media, L-glutamine in the form of a dipeptide, such as analyl-L-glutamine, glycyl-L-glutamine or protein hydrolyzates (e.g., gluten hydrolysate), may be used.

Another aspect of the present disclosure is a method for maintaining an optimal glucose level in a cell culture by providing the culture with a pH-sensitive hydrogel that includes glucose under conditions where the glucose is released into the cell culture in response to a change in the cell culture pH, such that the optimal level of glucose in the culture is maintained. In one embodiment, the optimal range for glucose levels in a culture is from 3.0 to 5.5 g/L. In another embodiment, the optimal range for glucose levels in a culture is 3.0 to 4.5 g/L. In yet another embodiment, the optimal range for glucose levels in a culture is 4.0 to 5.5 g/L. Embodiments of the present disclosure feature methods for maintaining an optimal glucose level in a cell culture wherein the lower level for an optimal glucose level range is a value between about 1.0 and 4.0 g/L (e.g., about 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 g/L) and wherein the upper level for an optimal glucose level range is a value between about 3.0 and 10.0 g/L (e.g., about 3.0, 3.1, 3.2, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 and 10.0 g/L).

Another aspect of the present disclosure is a method for maintaining an optimal L-glutamine level in a cell culture by providing the culture with a pH-sensitive hydrogel of the present disclosure that includes L-glutamine, as free L-glutamine or in a more stable and preferably readily available form, under conditions where the L-glutamine is released into the cell culture in response to a change in the cell culture pH, such that the optimal level of L-glutamine in the culture is maintained. In one embodiment, the optimal range for L-glutamine levels in a culture is from 1.0 to 10.0 mM. In another embodiment, the optimal range for glucose levels in a culture is 2.0 to 4.0 mM. Embodiments of the present disclosure feature methods for maintaining an optimal L-glutamine level in a cell culture wherein the lower level for an optimal L-glutamine level range is a value between about 1.0 and 2.0 mM (e.g., about 1.0, 1.2, 1.3, 1.4, 1.5, 1.6, 1.7, 1.8, 1.9 and 2.0 mM) and wherein the upper level for an optimal L-glutamine level range is a value between about 4.0 and 10.0 mM (e.g., about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 and 10.0 mM).

Hydrogels of the present disclosure are used to deliver one or more agents to a cell culture, where the hydrogels are comprised of cross-linked polymer networks formed from a pH-sensitive precursor, a linker or cross-linker and one or more agents for delivery, so that the pH-responsiveness of the polymer network results in a change in the rate of release of one or more agents and/or buffers. Additional aspects of the present disclosure are hydrogels that have pH-responsive polymer networks that respond by becoming more swellable or less swellable. An additional aspect of the present disclosure includes hydrogels that include, as one or more agents for delivery, a pH-sensitive dye, glucose, amino acids, growth factors, a cell media pH-regulating agent and/or buffer. Additional aspects of the present disclosure also include hydrogels with hydrophilic pH-sensitive compounds with one or more groups subject to reactive inclusion in a polymer network.

In one aspect, the present disclosure relates to a pH-responsive polymer for delivering one or more agents to a cell culture, comprising a pH-sensitive precursor, a linker or cross-linker, and the one or more agents, wherein the pH-sensitive precursor and the linker or cross-linker form a cross-linked polymer network, wherein the pH-sensitive precursor comprises more than two amine hydrogens on average and the linker or cross-linker comprises at least two epoxy groups on average, or the pH-sensitive precursor comprises at least two amine hydrogens on average and the linker or cross-linker comprises more than two epoxy groups on average, and wherein pH-responsiveness of the polymer network results in a change in the rate of release of one or more agents, or the rate of uptake of absorbed or scavenged components. The one or more agents may be selected from the group consisting of a pH-sensitive dye, glucose, amino acids, growth factors and a cell media pH-regulating agent and buffer.

In another aspect, the present disclosure relates to a method for delivering one or more agents to a cell, comprising the steps of adding a pH-responsive polymer to a media comprising the cell, wherein the polymer is capable of releasing the one or more agents into the media, culturing the cell in a under conditions wherein the one or more agents is released into the media, and delivering the one or more agents to the cell.

In another aspect, the present disclosure relates to a method for maintaining an optimal cell culture pH, comprising the steps of adding a pH-responsive polymer to the cell culture, wherein the one or more agents comprises a pH-regulating agent or buffer, and wherein the polymer is capable of releasing the pH-regulating agent or buffer into the cell culture, culturing the cell under conditions wherein the pH-regulating agent or buffer is released into the cell culture in response to a change in the pH of the cell culture, and maintaining the optimal cell culture pH. In one embodiment, the pH-sensitive precursor may be the agent released from the pH-responsive polymer that maintains the optimal cell culture pH.

In another aspect, the present disclosure relates to a method for maintaining an optimal cell culture glucose level, comprising the steps of adding a pH-responsive polymer to the cell culture, wherein the one or more agents comprises glucose, and wherein the polymer is capable of releasing the glucose into the cell culture, culturing the cell culture under conditions such that the glucose is released into the cell culture in response to a change in the pH of the cell culture, and maintaining the optimal cell culture glucose level.

In another aspect, the present disclosure relates to a method for maintaining an optimal cell culture L-glutamine level, comprising the steps of adding a pH-responsive polymer to the cell culture, wherein the one or more agents comprises L-glutamine and wherein the polymer is capable of releasing the L-glutamine into the cell culture, culturing the cell culture under conditions such that the L-glutamine is released into the cell culture in response to a change in the pH of the cell culture, and maintaining the optimal cell culture L-glutamine level. The agent may comprise L-glutamine in the free form or as a more stable form, such as a dipeptide (e.g., analyl-L-glutamine or glycyl-L-glutamine) or protein hydrolyzate (e.g., gluten hydrolysate).

In another aspect, the present disclosure relates to a method of preparing a pH-responsive polymer, comprising the steps of providing a pH-sensitive precursor, and mixing the a pH-sensitive precursor with a linker or cross-linker to form the polymer, wherein the pH-sensitive precursor comprises more than two amine hydrogens and the linker or cross-linker comprises at least two epoxy groups on average or the pH-sensitive precursor comprises at least two amine hydrogens and the linker or cross-linker comprise more than two epoxy groups on average. The formulation of the polymer may occur in the absence of a solvent.

An additional aspect of the present disclosure is a method of non-invasive measurement of the pH level of a cell culture, by providing a hydrogel with a pH-sensitive dye, passing light through the cell culture, measuring the absorbance of light by the cell culture at one or more wavelengths that correspond to one or more absorption spectra of the pH-sensitive dye and determining the pH reading for the culture using the measurements of the absorbance of light by the cell culture. A further aspect of the present disclosure features an apparatus for determining pH of a cell culture in a non-invasive fashion that has one or more light sources, one or more optical fibers for directing light from the light source(s) to the cell culture, one or more lenses for focusing light after it has passed through the cell culture, one or more optical filters that select one or more light wavelengths, one or more photodetectors that can measure the amount of light that has passed through the one or more filters, and a computational device that can generate a pH measurement based on the ratio of light absorbance calculated by the photo detectors. Embodiments of the present disclosure feature methods of non-invasive measurement of the pH level of a cell culture, by providing a hydrogel with a pH-sensitive dye that allows visual inspection of the hydrogel for changes in color indicative of changes in pH.

An additional aspect of the present disclosure is a method of non-invasive measurement of the pH level of a cell culture, by providing a hydrogel with a pH-sensitive dye, directing light (or radiation) to or through a cell culture and visually observing, or measuring, of the hydrogel under an appropriate source of illumination to ascertain qualitative changes in pH via changes in hydrogel coloration, fluorescence or luminescence. In some embodiment, such as using fluorescence, an additional non-pH sensitive dye may be used as a standard to correct the absolute intensity which may vary as a function of temperature, photobleaching, etc.

BRIEF DESCRIPTION OF THE DRAWINGS

FIGS. 10-12 show Tables 1-3 which list specific embodiments of the present disclosure and characteristics of each embodiment.

FIG. 13 shows Table 4 which lists the pH and glucose responses in DMEM medium of different hydrogel polymer embodiments of the present disclosure.

FIGS. 14 and 15 show Tables 5 and 6 which list pH and glucose calculated responses for the hydrogel polymers in cell culture media.

DETAILED DESCRIPTION OF THE INVENTION

Figure 1:
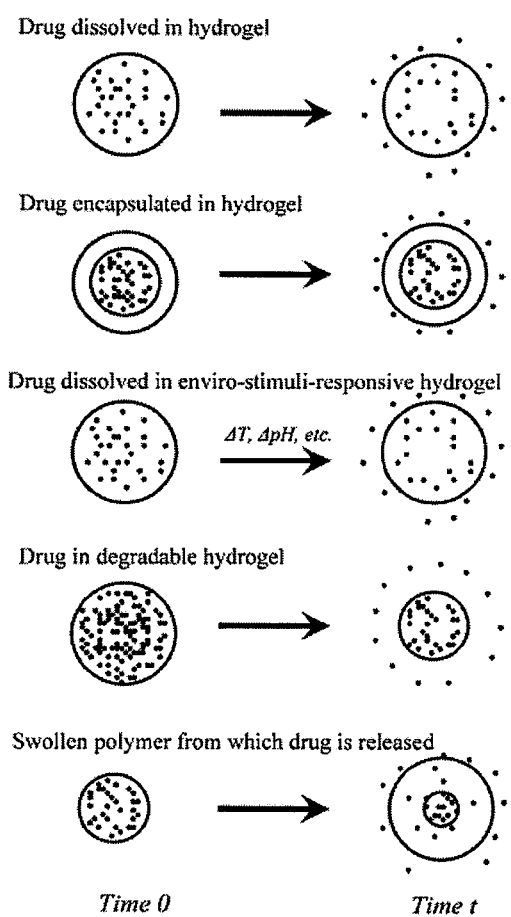
FIG. 1 shows various means by which hydrogels may deliver compounds to the surrounding environment.

Hydrogels of the present disclosure feature responsive hydrogels that release and/or allow the permeation of desired compounds (e.g., nutrients, buffers, therapeutic and/or bioactive agents, etc.) in response to changes in the environment (e.g., pH, temperature, the concentration of ions and/or other molecules). In a preferred embodiment, a pH-sensitive hydrogel serves as a non-invasive, real-time vehicle for delivering key cell culture media components. In preferred embodiments, hydrogels of the present disclosure serve to both deliver compounds to a cell culture media and absorb/scavenge components from a cell culture media. The present disclosure also relates to the long-term support of cell growth.

The present disclosure encompasses hydrogels that provide beneficial effects when used in cell culture systems. Some hydrogels of the present disclosure provide compounds in response to changes in cell culture media. Compounds provided by the hydrogels may include nutrients consumed by cells in the culture, compounds that change characteristics of the cell culture media and compounds that restore original conditions in the cell culture media that have changed over time or with cell growth in the media, or that maintain conditions in the cell culture media that would otherwise have changed over time or with cell growth in the media, or that substantially attenuate the rate at which such changes occur. Changes in various parameters of cell culture media are often correlated with one another. For example, certain culture parameters, such as glucose consumption, may be correlated with changes in culture pH levels. As cells consume glucose, cells produce lactic acid, and the pH of mammalian cell cultures will decrease over time in response to the concentration of lactic acid produced. Eventually, the glucose supply is exhausted and must be replenished by some means if the culture is to remain viable. This holds true for other key nutrients, such as glutamine and other amino acids.

Thus it is necessary to both maintain the pH of the culture at an optimal level and to periodically replenish key nutrients. This may be achieved in a variety of ways, including via automated methods, but for small-scale cell culture (<1 L) this is typically done by manually determining pH/nutrient levels and making additions as necessary. Time and personnel constraints generally restrict monitoring of cultures to one or two time points within a twenty-four hour period. When approached in this manner, the cells may spend several hours in sub-optimal conditions that may lead to a decrease in growth and loss of function. It is therefore desirable to make these adjustments in as close to a real-time manner as possible. However, automated cell-monitoring/culturing systems are generally expensive and require specialized instrumentation. In a preferred embodiment, the hydrogels of the present disclosure are for use with cell cultures that require monitoring and potential adjustments every 4, 8, 12, 16, 20, 24, 36 and/or 48 hours.

Hydrogels of the present disclosure provide a new method of cell culture maintenance. Certain hydrogels are pH sensitive, swelling in response to decreased pH and shrinking when the pH level increases. Some embodiments of the present disclosure feature a pH-sensitive hydrogel suitable for use in mammalian cell culture that can be made to incorporate compounds such as nutrients and/or pH buffers. As the culture pH drops, such hydrogels will release nutrients and take up or neutralize acid and/or release buffers or alkaline species. This increases the culture pH, which causes the gel to deswell and produces a slowing or cutting off of continued release, until such time as the pH of the culture again drops below a predetermined critical level. It is herein demonstrated that the nature of the environmental response (in this case, to changes in pH) can be tuned based on the composition and architecture of the hydrogels of the present disclosure, and that highly desirable pHs can be maintained within about 0.02 pH units of a desired pH reading for over a week using these materials, in addition to showing that they are capable of releasing glucose and enhancing cell growth as a result during this time. In preferred embodiments, cell culture pH values can be maintained within about 0.10 pH units of a pH of, for example, 7.05 for up to a week. More preferably, the cell culture pH values can be maintained within about 0.05 pH units for up to a week. Most preferably, the cell culture pH values can be maintained within about 0.02 pH units for up to a week.

In addition to the aforementioned environmentally responsive swelling/deswelling behavior found in some embodiments of the present disclosure, a number of additional functions may be readily added to hydrogels of the present disclosure, due, at least in part, to the versatile materials chemistries employed in its production. As described, bioactive agents such as inhibitors and promoters may be added, allowing regulation of protein expression. Likewise, hydrogels of the present disclosure are easily surface functionalized to affect the adhesion of cells and/or small molecules on their surfaces. The incorporation of environmentally sensitive dyes (e.g., responding to pH, the concentration of ions or molecules, temperature, etc.) is also possible, either in bulk or solely at the surface and either via physical absorption/entrapment of the dyes or chemical bonding, so as to enhance response time and avoid any averaging of environmental conditions as indicated through changes in the dye's optical spectra. In additional embodiments, one or more agents, including dyes, can be added to and/or leached from hydrogels of the present disclosure to create hydrogels with uniform agent concentrations throughout the gel, with a gradient of agents by location within the gel or with a localization of agents to one or more particular locations or regions of a hydrogel. The chemistry and architecture of the hydrogel may also be engineered to "recognize" molecular or ionic species and allow some to pass through while preventing others from doing so, based on size, charge, content or any other parameter of molecular identity or function. In some aspects, hydrogels of the present disclosure permit real-time adjustments to mammalian cell culture, thereby maintaining the health of the culture with a minimum of human intervention and significantly decreasing the risk of contamination and the man-hours required to maintain cells under standard culturing techniques. In one embodiment, a comprehensive system for achieving these goals comprises at least two discrete elements. The first is a pH sensitive hydrogel that is designed to deliver key nutrients based on changes in culture pH and is coupled with a pH sensitive dye. The second element of this system is a transmission-spectrum based pH detection system, which will permit online, non-invasive pH measurement of cell cultures. The second element of this system is described in Section III below. In another embodiment, a pH sensitive hydrogel that is designed to deliver key nutrients based on changes in culture pH is coupled with a pH sensitive dye to allow for visually evident color changes as an indication of culture pH. Alternatively, the comprehensive system may consist of the two discrete elements provided above.

In one embodiment, the present disclosure relates to a pH-responsive hydrogel polymer for delivering one or more agents to a cell culture, comprising a pH-sensitive precursor, a linker, and one or more agents, wherein the pH-sensitive precursor and the linker are covalently attached to each other, wherein the pH-sensitive precursor comprises an average functionality of more than two amine hydrogens per molecule and the linker comprises an average functionality of at least two epoxy groups per molecule, or the pH-sensitive precursor comprises an average functionality of at least two amine hydrogens per molecule and the linker comprises an average functionality of more than two epoxy groups per molecule, and wherein the one or more agents is released into the cell culture in response to a change in the cell culture pH.

Definitions

In order that the present disclosure may be more readily understood, certain terms are first defined.

In general, the term "hydrogel" relates to a water-swollen polymeric material that maintains a distinct structure. More typically, hydrogels, also referred to as (super-) absorbent polymers (SAP) or absorbent gelling materials (AGM), are water-insoluble, water- or aqueous media-swollen, cross-linked polymeric structures that are produced by reactions of monomers and/or polymers and often take the form of three-dimensional insoluble polymer networks. Hydrogels composed of hydrophilic polymers can often absorb up to thousands of times their dry weight in water or aqueous media. As a general category of materials, hydrogels have been put to a myriad of uses in medicine, bioengineering and scientific research. For example, hydrogels have been used to create bioadhesive carriers for drug and compound delivery and to develop implant coatings and materials to assist in wound healing.

A polymer network of the present disclosure may contain liquid matter or may be essentially dry. The hydrogels of the present disclosure may comprise water, i.e. they are essentially not devoid of water, or an aqueous solution of interest or otherwise relevant to the cell culture. Likewise, the hydrogel polymer networks of the present disclosure are essentially not devoid of water or aqueous matter, but can absorb water upon exposure to water or an aqueous solution. As used herein, a "solvogel" refers to a polymer network that comprises a solvent, i.e. that is not essentially devoid of liquid. As used herein, a "xerogel" refers generally to an unswollen polymer network.

The term "expansion" as used herein refers to a change in shape and/or volume of an object that leads to the object occupying a larger or a different space that it did previously. In preferred embodiments, a hydrogel of the present disclosure will expand in response to a change of conditions. For example, a hydrogel of the present disclosure may expand as a result of a change of pH or a change in immediate surroundings, such as a transfer from a gaseous to a liquid environment. The expansion may be due to a static property of the hydrogel or may be due to a property of the hydrogel that is created by the change of conditions.

The term "swellable" as used herein refers to the ability of a hydrogel to expand, either due to static properties of the hydrogel or a subset of its components or due to properties of a hydrogel or a subset of its components that are created by a change of conditions, wherein the hydrogel takes up material from its surroundings as it expands and/or the hydrogel becomes more permeable. Upon swelling or entering a swelled state, properties of the hydrogel may change. Changes in hydrogel properties may include a change in the rate of release of a component of the hydrogel or a change in the rate of absorbance of molecules from the surrounding material.

The terms "precursor" or "polymer precursor" as used herein refer to any monomer or polymer molecular species that can be polymerized to form a polymer network of the present disclosure. As such, a solution containing one or more precursors may contain a chemical species comprising one subunit of a polymer compound (i.e., a monomer) or two or more subunits covalently linked with each other. In preferred embodiments, a precursor for use in creating polymer networks of the present disclosure will have at least two reactive groups per molecule. In other embodiments, a precursor for use in creating polymer networks of the present disclosure will have more than two reactive groups per molecule on average. In some embodiments, a precursor may have an essentially linear structure. In other embodiments, a precursor may have a branched structure, comprising at least one branch point from which two or more portions of the precursor molecule originate.

The term "linker" as used herein refers to a component added to a reaction mix containing at least one precursor, in order to form a polymer network of the present disclosure based on reactions between reactive groups in the linker and reactive groups in the precursor. In preferred embodiments, a linker will contain at least two reactive groups (i.e. groups capable of reacting with precursor reactive groups) per molecule. In more preferred embodiments, a linker will be a "cross-linker", i.e. will comprise more than two reactive groups per molecule on average and will be able to link to more than two reactive groups present on precursor molecules. Exemplary linkers include, but are not limited to, polyfunctional epoxy linkers/cross-linkers, used, for example, to link polyfunctional precursors.

The term "cross-link" as used herein refers to connections between molecules of the polymer network wherein a molecule is, on average, bound or physically associated with two or more other molecules of the polymer network simultaneously. In preferred embodiments, a polymer network of the present disclosure comprising at least one cross-link can be created using a cross-linker. In some embodiments of the present disclosure, a polymer network comprising at least one cross-link can be created by using a linker with two reactive groups with at least one precursor comprising at more than two reactive groups on average. The term "cross-linker" as used herein refers to a linker comprising at least two reactive groups on average.

The term "reactive group" as used herein refers to a portion or moiety of a first molecule that is chemically reactive (i.e. capable of forming chemical bonds) with a portion or moiety of a second molecule found in the reaction mix. In preferred embodiments, at least two types of reactive groups or moieties can be found in the reaction mix and a reaction can take place between groups or moieties of the two types, leading to a covalent or ionic bond that serves to support the structure of the polymer network of the present disclosure. In one preferred embodiments, one type of reactive group in the reaction mix is an epoxy group and a second type of reactive group is an amine group. In some embodiments, primary epoxy groups are preferred over secondary epoxy groups. In other embodiments, secondary epoxy groups are favored. Preferably, the amine group comprises amine hydrogen(s) (e.g., primary and/or secondary amine groups).

As used herein, the term "functional group" refers to a portion or moiety (e.g., a group of atoms) of a molecule or substance that imparts a function (e.g., a chemical behavior) on the molecule and may impart a function on a polymer network of which the molecule is a part. Often the functional groups of an organic molecule are the non-hydrocarbon portions of moieties of said molecule. A functional group may be a reactive group if the functional group can react with another molecule (or functional or reactive group thereof) to form a chemical bond between the molecules or groups.

As used herein, the term "epoxy" refers to a functional group of atoms comprising a primary epoxide or a secondary epoxide. A primary epoxide is shown below.

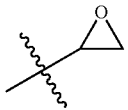 [SMILES: *C1CO1]

In particular embodiments, any organic compound which contains an epoxy group may also be referred to briefly as an "epoxy". An epoxy may have more than one epoxy group. An epoxy that has two or more epoxy groups may be known as "polyfunctional". An epoxy that has two epoxy groups may be known as a "diepoxide". An epoxy that has three epoxy groups may be known as a "triepoxide", etc.

The term "link" or "linkage" as used herein refers to an association between two or more molecules, groups or moieties thereon. In preferred embodiments, "link" or "linkage" refers to a chemical bond between two or more molecules. In more preferred embodiments, "link" or "linkage" refers to a covalent bond between two or more molecules.

As used herein, the term "branched" refers to the structure of a precursor, linker or cross-linker, wherein the molecule does not have an essentially exclusively linear structure.

As used herein, an "epoxy-amine" link refers to a link between molecules formed by a reaction between two or more molecules in the reaction mix, wherein the link comprises the following structure:

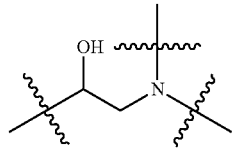 [SMILES: *C(O)CN(*)*]

Alternatively, the epoxy-amine link may be referred to as an imine linkage (i.e. —C—N—C—).

As used herein, the term "junction point" refers to a location in a polymer network that marks one end of a substantially linear segment of a molecule. In some embodiments, "junction point" refers to a location where a linker or cross-linker becomes linked to another molecule or molecules of the polymer network. In some embodiments, "junction point" may refer to a location where a branch of a branched precursor is attached to another part of the precursor. In preferred embodiments, a "junction point" is a location where a reaction occurred during the formation of the polymer network between a reactive group on a linker or cross-linker and a reactive group on a precursor.

The term "dye" as used herein comprises chemical compounds that have the ability to absorb, alter or change the wavelengths of light that passes through, or is incident upon, a composition that comprises them (e.g., compounds for absorbance, luminescence, fluorescence and/or phosphorescence). The term "dye" includes the use of optically active nanoparticles. This ability itself may change, start or stop as conditions in the composition change, constituent molecules of the composition are introduced or removed or constituent molecules of the composition increase or decrease in number or concentration.

As used herein, the term "extended period of time" refers to an amount of time that is greater than the amount of time during which optimal cell culture conditions last in a standard cell culture set-up comprising cells and cell culture media, i.e. without a hydrogel of the present disclosure.

The terms "responsive" and "responsiveness" as used herein refer to the ability, in preferred embodiments, of hydrogels to react to a change in their local environments. The change in the local environment of the gel may comprise a change in pH, in temperature, in the physical state of the surrounding material (e.g., gas to liquid) or a change in the ratio or presence of one or more molecular or ionic species in the surrounding material. The change in the local environment may be a change within the hydrogel of the present disclosure itself. The reaction to a change in the local environment undergone by hydrogels of the present disclosure comprises changes in the molecular composition of the hydrogel or one of its components, changes in the structure of the hydrogel, and changes in the size of the hydrogel, which can be on a macroscopic and/or microscopic level. The reaction to a change in the local environment of a hydrogel of the present disclosure can comprise a change in a property of a hydrogel, such as the hydrogel becoming more permeable to a molecular species within the hydrogel or in the surrounding material, or the hydrogel becoming less permeable to a molecular species within the hydrogel or in the surrounding material. This may lead to the hydrogel releasing and/or scavenging molecular or ionic species to and/or from the surrounding environment, and/or doing so at a higher rate.

The term "pH-sensitive", as used herein, refers to a molecule or molecular species found within a hydrogel of the present disclosure and/or in the surrounding material that will experience a change in form, structure, state and/or properties when a change in the pH of the hydrogel or the surrounding material occurs.

The term "pH regulating", as used herein, refers to a molecule or molecular species that is capable of causing a change in the pH level of an aqueous solution when it enters the solution or when it is contacted with a molecule or a molecular species from the aqueous solution.

Hydrogels of the present disclosure may be characterized by their "mesh size", a term which, as used herein, describes characteristics of the hydrogel in terms of the spatial relationships between molecules comprising the hydrogel. Mesh size may change in response to a change in the local environment. In preferred embodiments, hydrogels of the present disclosure comprise an arrangement between polymers, linkers and/or cross-linkers, which assemble into a regular or semi-regular latticework during the formation of the hydrogel. The arrangement between polymers, linkers and/or cross-linkers in a hydrogel of the present disclosure may be described with or may be considered a component of the hydrogel's mesh size. Other aspects of mesh size can relate to the hydration of the gel and the state of protonation of an element or species in the hydrogel. Generally, in preferred embodiments, mesh size can be related to the interaction of the hydrogel with its surrounding material. Responsiveness of a hydrogel may include a change in the mesh size of the material of a hydrogel of the present disclosure and such a change may be a component of a change in the permeability of a hydrogel of the present disclosure.

In one embodiment, the distribution of mesh sizes present in the hydrogel may be such that both small molecules to be delivered and small molecules to be absorbed may pass through the mesh at some or all pH values. The contour length of polymer chains between consecutive crosslinks determines the maximum mesh size when the material is fully swollen and all chains are extended to their maximum extent. The crosslinks may be chemical or physical; the latter can include entanglements which can move. The shape of the mesh size distribution affects the exact value. Very small mesh sizes can exclude molecules of interest for delivery/absorption from the network and/or substantially limit swelling. Likewise, the distribution of mesh sizes present in the hydrogel should be such that changes in pH induce a measurable difference in delivery and/or uptake kinetics. Very large mesh sizes can lead to hydrogels that are able to swell so significantly in water, independent of pH, that pH-dependent changes would be minimized and mechanical stability of the hydrogels compromised as a result. In one embodiment, the mesh size of the hydrogel polymer of the present disclosure is effectively zero when the network is not swollen or comprises not additional components or agents. The incorporation of additional components or agents swells the hydrogel, at least locally. In one embodiment, the product of contour length and relative swelling (i.e. swelling normalized to the maximum degree of swelling that may be realized in a given network) is one way to estimate mesh size.

As used herein, the term "absorbance" can refer to the movement of a molecule from the surrounding material into a hydrogel of the present disclosure. The terms "absorb" and "scavenge" refer to the ability of hydrogels of the present disclosure to take up materials from cell culture media, such as acidic by-products of cell metabolism, toxic substances originating from cells or molecules originating from the environment surrounding the cell culture. The term "absorbance" may also include the temporary retention of energy by a hydrogel of the present disclosure. For example, in preferred embodiments, a hydrogel of the present disclosure may retain electromagnetic energy in the form of a particular wavelength of light. The capacity of a hydrogel of the present disclosure to absorb a molecule or energy may be a characteristic of a molecular species that forms the structure of the hydrogel or may be a characteristic of a molecular species that the hydrogel comprises, such as a molecule that was added after the formation of the gel. In preferred embodiments, an example of such a molecule may be a pH-sensitive dye molecule.

The production of a hydrogel involves the formation of a network consisting of polymer chains and junction points, e.g., links or cross-links, between these chains. Without wishing to be bound by any particular theory, it is believed that this cross-linking prevents or impedes dissolution of the polymer by keeping the chains in place relative to the hydrogel. Because of the hydrophilic nature of at least some of the polymer chains, such materials will exhibit substantial swelling when immersed in water, thus producing a hydrogel.

In terms of compound delivery, there are a number of potential delivery mechanisms that may use a hydrogel to deliver an active agent. Most generally, however, compound delivery takes advantage of either diffusion of the agent out of the hydrogel (the simple case) or environmentally induced changes in the swellability of the hydrogel that induce release of the active agent (the responsive case). An overview of the major compound release mechanism is shown in FIG. 1. Responsive polymers are especially useful for compound delivery applications in that, with proper engineering of the hydrogel, release can be controlled to occur at a desired time or during a desired interval.

Hydrogels that are formed from polymers containing functional groups that are acidic tend to show low swelling (and release) under acidic conditions and high swelling (and release) under alkaline conditions. Polymers containing functional groups that are basic tend to show the opposite trend. Finally, polymers whose solubility is due primarily to weak and easily disrupted hydrogen bonds with water tend to show much lower degrees of swelling when heated above the critical temperature necessary to break the aforementioned hydrogen bonds, which renders them partially or completely insoluble.

Dyes used for "real-time" optical determination of pH via pH sensitive dyes are often incorporated into a dedicated sensor, whereas in certain embodiments of the present disclosure, the method of the present disclosure will incorporate the dye into the hydrogel system itself. In one embodiment, the change in pH can be detected by placing the cell culture vessel, containing the hydrogel, into a sensing unit that employs the transmission method to measure pH with a reversible dye in the hydrogel. The pH indicator dye is pH sensitive in absorption spectrum or color. When the dye is dissolved in a solution, it will generate two molecular species with two different colors, respectively. The relative concentration of these two species, or the ratio of them, which is determined by the pH of the solution, determines the overall color of the solution. In another embodiment, the change in pH can be detected by visual observation of a change in the color of the hydrogel.

Hydrogels of the present disclosure can be formulated with polymers or polymeric side chains that will react to changes in cell culture media. For example, hydrogels of the present disclosure can be formulated with particular polymers that will lead to swelling of the hydrogel in response to changes in the pH of cell culture media. In particular, some hydrogels with basic side-chain residues will swell in response to acidic conditions and thereby become more permeable to agents within the gel matrix and to compounds in the media. This increase in permeability can lead to an induction of compound release or absorption or an increase in the rate of compound release or absorption to or from the hydrogel.

Precursors

Hydrogels of the present disclosure can be made from a variety of precursors, including monomers and polymers. Some hydrogels of the present disclosure are made from synthetic polymers (e.g., PEGs), featuring a high water content and biocompatibility with low degradability. Some polymers may in general be non-ionic, cationic, zwitterionic, or anionic. In some embodiments, polymers are cationic or anionic.

Particular hydrogels of the present disclosure feature polymer networks that do not dissolve or degrade in aqueous solutions and may feature networks composed of polymer chains interspersed with junction points, links and/or cross-links. Some hydrophilic hydrogels of the present disclosure substantially swell when placed in water or aqueous media. In preferred embodiments, no custom synthesis of precursors is required as off-the-shelf, commercially available precursors are used.

In some embodiments, hydrogels include acid polymers, which contain a multiplicity of acid functional groups such as carboxylic acid groups, or their salts, preferably sodium salts. Examples of acid polymers suitable for use herein include those which are prepared from polymerizable, acid-containing monomers, or monomers containing functional groups which can be converted to acid groups after polymerization. Such monomers include olefinically unsaturated carboxylic acids and anhydrides, and mixtures thereof. The acid polymers can also comprise polymers that are not prepared from olefinically unsaturated monomers, including polysaccharide-based polymers such as carboxymethyl starch and carboxymethyl cellulose, and poly(amino acid) based polymers such as poly(aspartic acid). Poly(amino acid) absorbent polymers can be found, for example, in U.S. Pat. No. 5,247,068.

In some embodiments, some non-acid monomers may be included, e.g., in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. Non-acid monomers can be found, for example, in U.S. Pat. Nos. 4,076,663 and in 4,062,817.

Olefinically unsaturated carboxylic acid and anhydride monomers useful herein include the acrylic acids typified by acrylic acid itself, methacrylic acid, alpha-chloroacrylic acid, alpha-cyanoacrylic acid, beta-methylacrylic acid (crotonic acid), alpha-phenylacrylic acid, beta-acryloxypropionic acid, sorbic acid, alpha-chlorosorbic acid, angelic acid, cinnamic acid, p-chlorocinnamic acid, beta-stearylacrylic acid, itaconic acid, citroconic acid, mesaconic acid, glutaconic acid, aconitic acid, maleic acid, fumaric acid, tricarboxyethylene, and maleic anhydride.

In some embodiments, hydrogel forming polymers contain carboxyl groups, such as the above-described carboxylic acid/carboxylate containing groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network cross-linked polymers of any of the foregoing copolymers, polyacrylic acid, and slightly network cross-linked polymers of polyacrylic acid, as well as mixtures of any one or more of the above polymers. Examples of these polymer materials are disclosed, for example, in U.S. Pat. Nos. 3,661,875, 4,076,663, 4,093,776, 4,666,983, and 4,734,478.

The hydrogel forming polymers useful in the present disclosure can be formed by any polymerization and/or cross-linking techniques. Such techniques are known in the art, e.g., as described in U.S. Reissue Pat. 32,649, U.S. Pat. Nos. 4,666,983, and 4,625,001, 5,140,076, 6,376,618, 6,391,451, 6,239,230 and 6,150,469. Cross-linking can be effected during polymerization by incorporation of suitable cross-linking monomers. Alternatively, the polymers can be cross-linked after polymerization by reaction with a suitable reactive cross-linking agent. Without wishing to be bound by any particular theory, it is believed that surface cross-linking of the initially formed polymers may control the absorbent capacity, porosity and permeability of the resultant hydrogel.

Hydrogels may be made with a combination of two or more different monomers or polymers, from similar or different sources (i.e. a mixture of synthetic and natural polymers), such as a collagen-acrylate hydrogel). The hydrogels may comprise modified cellosics, such as hydroethylcellulose or hydroxypropylcellulose, polysaccharides, such as pullulan or deacetylated chitosan, poly(vinyl alcohol) or poly(allyl alcohol), poly(vinyl amine), poly(allylamine), poly(vinyl acetate), poly(vinyl formamide), poly(2-ethyloxazoline) and linear poly(ethyleneimine), or mixtures thereof. Theses materials include some that are pH-sensitive and pH-insensitive. For poly(vinyl acetate) and poly(vinyl formamide), these materials may be partially hydrolyzed.

In certain aspects, the hydrogels of the present disclosure feature polyfunctional epoxy cross-linkers in combination with di- or poly-amine-functional compounds to form epoxy-amine networks. Preferred hydrogels of the present disclosure include gels formed of hydrophilic epoxy derived networks or matrices. Hydrogels of the present disclosure may comprise polymer networks featuring epoxy-amine linkages. In some embodiments, a suitable organic solvent is used to create a solution of one or more components of a reaction mix and/or is used as a component in the reaction mix. In other embodiments, the components of the reaction mix are liquid and no solvent is present. Depending on the formula of the hydrogel (e.g., the particular polymer(s) used as ingredients), hydrogels of the present disclosure may have different hydrophilic properties. Additionally, they may be reactive or unreactive to changes in the cell culture media. Some hydrogels of the present disclosure react to changes in the pH of the media. In particular, some hydrogels will swell in reaction to the development of a more acidic pH in the media. In some embodiments, a choice of a particular linker or cross-linker may affect the properties of the hydrogel after formation.

The hydrogels of the present disclosure may comprise PEG diglycidyl ether, branched PEG polyglycidyl ether, PEG diamine, branched PEG polyamine, PEG copolymer having (di or poly)-glycidyl ethers or (di or poly) amines, e.g., Jeffamine® ED materials which comprise PPO-PEO-PPO diamines, or mixtures thereof. The hydrogel may also comprise PEGylated small molecules or polymers that contain at least two amine or epoxy groups. For instance, a PEGylated poly(hydroxyethyl methacrylate) or poly(glycidyl methacrylate) treated with epichlorhydrin. The hydrogels may also comprise poly(ethyleneimine) or poly(2-ethyloxazoline) in place of PEG in the above examples. In certain embodiment, PEO segments may be replaced with less hydrophilic PPO or PTMO (poly-tetramethylene oxide) segments.

The hydrogels may also comprise poly(vinyl alcohol), poly(vinylamine), poly(allylamine), hydrophilic acrylates, methacrylates, acrymamides, methacrylamides, or mixtures thereof. These material may function as hydrophilic segments of the hydrogel In another embodiment, a hydrogel of the present disclosure has a hydrogel composition created through the formation of a hydrophilic polymer network. In some embodiments, a suitable organic solvent may be used. In other embodiments, a hydrogel of the present disclosure comprises a precursor segment that can exist as a charged or uncharged element. In preferred embodiments, precursor segments comprised by a hydrogel will exist in a cationic and hydrophilic state or a non-charged, less hydrophilic state, depending on the local environment of the hydrogel. In a more preferred embodiment, the local environmental condition influencing the state of a precursor segment of a hydrogel is the pH level of the local environment. A reactive, pH sensitive organic dye molecule is preferably included in this mixture as well, so that the final hydrogel will show pH-dependent optical properties (changes in color with changes in pH, for instance).

Examples of precursors that can exist as charged or uncharged molecules or elements of a polymer network include weak polyelectrolyte precursors. In some embodiments, weak polyelectrolyte precursors are not inherently cationic but may become so when the amine groups present in them are transformed into ammoniums (e.g., quaternized) by the introduction of acid ($H^+$), for example, through the production of acidic metabolites by the cells in a culture. Quaternization may also be carried out through other chemical reactions. Some embodiments of the present disclosure feature precursors that exist in an essentially permanently charged state.

In a preferred embodiment, the reactions between the precursor and linker/cross-linker requires no catalyst and is extremely rapid and robust, forming linkages that are expected to be stable under a wide range of conditions. Numerous reactive dyes with similar characteristics are commonly used in protein labeling and are therefore readily available.

In some embodiments, the precursor molecules contain epoxy-reactive functionalities, for example, primary or secondary amine groups and potentially other types of groups as well, such as hydroxyl groups, thiol groups, and/or carbonyl groups, such as carboxylic acid or carboxylic acid anhydride groups. Some of the precursors may also contain unreactive amine groups in regard to epoxy-reactive functionalities, for example, sterically-hindered, tertiary, or otherwise non-nucleophilic amine groups. The amine groups provide pH-sensitivity thanks to their ability to be protonated, and thus ionized, as their environment changes from neutral to acidic.

Linkers and Cross-Linkers

Embodiments of the present disclosure feature linkers and cross-linkers comprising one or more reactive groups.

In preferred embodiments, linkers and cross-linkers comprise epoxy groups. Epoxy groups can react with a number of different reactive groups. For example, a linker or cross-linker with an epoxy group may react with a precursor comprising an amine functional group to form an epoxy-amine linkage. If a linker or cross-linker comprising two or more epoxy groups is reacted with a precursor comprising two or more reactive groups such as amine groups (a polyamine), polymer networks and/or long polymer chains may be formed with epoxy-amine linkages.

Formation of Hydrogels

In preferred embodiments of the present disclosure, precursors and linkers/cross-linker, which may be either liquids, low-melting solids, or solutions comprising the same, are mixed and network formation proceeds spontaneously and rapidly at room temperature. Preferably, the formation of hydrogels of the present disclosure is performed at temperatures less than about 100° C. More preferably, the formation is performed at temperatures less than about 60° C. Some embodiments feature liquid precursors and/or cross-linkers. Preferred embodiments feature the use of commercially available, off-the-shelf precursors, linkers and/or cross-linkers in reaction mixes that require no potentially toxic catalysts or initiators. Some embodiments feature the use of a solvent, such as a polar, aprotic solvent. After formation, the polymer network may undergo solvent extraction, water immersion and/or loading procedures to incorporate compounds into the hydrogel. In the case that solvent is present, the solvogel created by the reaction may be dried by a variety of methods (e.g., at room temperature, under vacuum, in an oven) to create a xerogel, typically having a reduced volume as compared to the solvogel. In preferred embodiments, the hydrogel product is a chemically stable, physically robust, autoclavable solid that can be equipped with a range of desired functionalities and/or loaded with a variety of agents for delivery.

In some embodiments, the hydrogel of the present disclosure may be formed in the presence of other agents. In these embodiments, the linker/cross-linker and precursor are tolerant of the presence of water. As a result, it is not necessary to keep all reagents dry prior to the network formation. In these embodiments, the formation of the hydrogel may occur in solutions comprising other agents. For example, the other agents may comprise a pH-sensitive dye, glucose, amino acids, growth factors, a cell media pH-regulating agent and/or a buffer.

Preferred embodiments feature combinations of precursors and linkers/cross-linkers wherein at least one species in a reaction mixture comprises more than two reactive groups per molecule. Some preferred embodiments feature reaction mixtures comprising a cross-linker with three or more reactive groups. Some preferred embodiments feature reaction mixtures comprising a precursor with three or more reactive groups, for example, precursors containing multiple (i.e., more than three) amine hydrogens per molecule. One preferred embodiment features trifunctional epoxy cross-linkers combined with precursors with two or more reactive groups.

In other embodiments, the precursors comprising a central core comprising one or more low molecular weight aliphatic polyamines (e.g., ethylene diamine, diethylenetriamine, piperazine, among others) whose amine groups have been alkoxylated, with ethylene oxide and/or related cyclic ethers capable of ring-opening polymerization (e.g., propylene oxide and tetrahydrofuran, among others). Some embodiments feature one or more polyol-comprising hydrophilic poly(ethylene oxide) segments in combination with a pH-sensitive core.

Ingredients and Reaction Vessels

Hydrogels of the present disclosure may be synthesized from precursor, or a solution thereof in the presence of an organic solvent, that spontaneously forms polymer networks when mixed with one or more linker and/or cross-linker compounds, or a solution thereof. In regard to solutions thereof, typically, concentrations of precursors and linkers/cross-linkers in solution before polymerization range from 5 to 40% w/v (i.e. total solids concentrations from 5 to 40% in terms of mass of solids per volume of total solution) and may range from 1% to 80% or 0.1% to 100%. In preferred embodiments utilizing pure liquid ingredients, precursor and linker/cross-linker concentrations may be 100%. In a particular embodiment with 40% total solid concentration, preferred concentrations of precursors range from 15 to 95% of the total solid concentration, i.e. precursor concentrations range from 6 to 38% w/v. As the proportion of precursor in the total solid concentration rises, the proportion of linker/cross-linker ideally falls. Thus preferred concentrations of linkers/cross-linkers in this particular embodiment range from 85 to 5% of the total solid concentration, i.e. linker/cross-linker concentrations range from 34 to 2% w/v. In preferred embodiments, over the range of total solids concentrations from 5 to 40% w/v, precursor concentrations may range from 0.75 to 38% w/v and linker/cross-linker concentrations may range from 0.25 to 34% w/v. In more preferred embodiments, total solids concentrations range from approximately 1% to approximately 10% w/v.

In some embodiments of the present disclosure, amounts of precursors and linkers/crosslinkers are measured in terms of moles of reactive group per unit volume, typically in mmol per mL. In some embodiments, the total molar concentration of precursor reactive groups and of linker/cross-linker reactive groups may range from about 0.01 mmol/mL to about 50 mmol/mL. In preferred embodiments, total molar concentrations of precursor and linker/cross-linker reactive groups range from about 0.3 to about 15 mmol/mL, and more preferably from about 0.6 to about 12 mmol/mL. Individually, the molar concentration of reactive groups for either the precursor(s) or linker(s) range from about 0.005 to about 20 mmol/mL, preferably about 0.01 to about 15 mmol/mL, and more preferably about 0.15 to about 12 mmol/mL.

In other embodiments of the present disclosure, preferably in non-solvent systems, 0.3 mmol of precursor reactive groups are used with 0.3 mmol of linker/cross-linker reactive groups, for a total molar concentration of reactive groups in the reaction mix of 0.6 mmol. In some embodiments, molar concentration of precursor reactive groups and of linker/cross-linker reactive groups may range from 0.3 mmol to 12 mmol. In preferred embodiments, molar concentrations of precursor and linker/cross-linker reactive groups range from 0.3 to 12, from total molar concentration of reactive groups in a reaction mix of 0.6 to 24 mmol. In more preferred embodiments, molar concentration of precursor reactive groups and of linker/cross-linker reactive groups may range from 0.6 mmol to 6 mmol. In preferred embodiments, molar concentrations of precursor and linker/cross-linker reactive groups range from 0.6 to 6, from total molar concentration of reactive groups in a reaction mix of 1.2 to 12 mmol.

In preferred embodiments, amounts of precursor and linker/cross-linker for inclusion in reaction mixes are calculated on the basis of molar ratio of reactive groups. For example, in a reaction mix consisting essentially of two reactive species, a precursor with two reactive groups and a cross-linker with four reactive groups, the molar ratio would be 1:2. Molar ratios can be adjusted to achieve a desired stoichiometry in the reaction. Molar ratios in embodiments of the present disclosure may range between 1 to 100, 1 to 50, 1 to 20, 1 to 10, 1 to 5, 1 to 4, 1 to 3, 1 to 2, and 1 to 1 for ratios between reactive groups. Preferred embodiments of the present disclosure feature molar ratios between precursors and linkers/cross-linkers that range from 4:1 to 1:4. More preferably, molar ratios between precursors and linkers/crosslinkers of the present disclosure are approximately 2:1 to 1:2. Most preferably, molar rations between precursors and linkers/cross-linkers is approximately 1:1.

In preferred embodiments, linkers/cross-linkers for use to prepare the hydrogels of the present disclosure comprise at least one epoxy group; more preferably, linkers/cross-linkers comprise two or more epoxy groups. Within embodiments that comprise linkers/cross-linkers comprising multiple groups, preferred embodiments feature precursors comprising multiple reactive groups, such as amine hydrogens, and other groups.

The density of links and/or cross-links can substantially affect the mechanical properties of the hydrogels of the present disclosure. The link/crosslink density and the resultant mechanical properties of a hydrogel can best be manipulated through changes in the precursor concentration, linker/cross-linker concentration, and, if applicable, solvent concentration. Linkage/cross-linkage density can also be manipulated by selecting precursors and/or linkers/cross-linkers with different molecular weights or molecular architectures (i.e. branched vs. linear).

Selection of precursor can also be adjusted to manipulate parameters of the polymerization reaction in some embodiments. For example, the greater the functionality of the species in the reaction mix, the lower the degree of conversion required to form the network. In certain embodiments, the average molecular weight between links and/or cross-links can also substantially affect the mechanical properties.

In some embodiments of the present disclosure, suitable solvents for use in polymer formulations are those which are biocompatible, pharmaceutically acceptable, and will at least partially dissolve the polymeric or non-polymeric material. According to the present disclosure, the solvent has a solubility in aqueous medium, ranging from miscible to dispersible and is capable of diffusing into an aqueous solution or cell culture media. In addition, the solvent is preferably biocompatible.

If required, a solvent for use in the polymerization reaction mix is selected based on the solubilities of the precursor(s) and cross-linker(s). Preferred solvents for use with the present disclosure include aqueous and/or organic solvents, e.g., water or polar aprotic solvents and protic solvents. Preferred concentrations of the reagent in solvent range from 20% w/v to 80% w/v, more preferably 50% w/v to 80% w/v, for example, 75% w/v precursor in solvent.

In certain embodiments, there may be a preference for inert solvents that do not react with amine groups (e.g., halogenated hydrocarbons, esters and ketones are reactive with amines). In other embodiments, it may be useful to use solvents to moderate the reaction rate in the case of highly reactive systems, such as a solvent that disrupts hydrogen bonding or otherwise reversibly complexes with either reagent.

Gel formation can be made to occur in a wide range of reaction vessels, in terms of shape and size. Likewise, in some embodiments, gel adhesion can be engineered depending on the nature of the surface the gelling reaction mixture is in contact with. In this way a wide range of physical forms of the final product may be developed, from pellets (produced via gelation within non-adherent tubing following by sectioning) to large monoliths (via gelation in non-adherent reaction vessels that will be removed) to coatings (via gelation on or subsequent adhesion to an adherent surface) to supported gels (via gelation within an adherent reaction vessel that will be used as the final product). In particular embodiments, additional ingredients may be included within reaction mixes in order to adjust the speed of polymerization to a desired level.

Catalysts

Some embodiments of the present disclosure feature the addition of catalysts to the reaction mix. Catalysts featured in preferred embodiments of the present disclosure include catalysts that cause minimal toxicity, i.e. that cause a negligible or insubstantial amount of toxicity to cells in a cell culture, as a result of being a component of a reaction mix to create a polymer network of the present disclosure.

Some preferred catalysts of minimal toxicity are catalysts that can be easily removed from a hydrogel of the present disclosure because of their inherent high water solubility and/or high volatility. Examples of this type of catalyst include tertiary amines, such as triethylamine, DABCO, and DBU (1,8-Diazabicyclo[5.4.0]undec-7-ene). In preferred embodiments, triethylamine or DBU are used as catalysts.

Other Ingredients

Embodiments of the present disclosure comprise polymer network-forming reaction mixes comprising additional ingredients. Some ingredients for use with embodiments of the present disclosure comprise agents that alter the structure or architecture of the polymer network and/or the hydrogel. For example, certain precursor or linker component compounds can have monofunctionality (e.g., they contain only one functional group) and can be included in a reaction mix to form "dead-ends" (e.g., where the polymer network is interrupted). Monofunctional precursors and linkers may also be used to reduce link and/or cross-link density. Additional compounds can be added to embodiments of the present disclosure in order to introduce functionalities to the hydrogel of the present disclosure. Examples of such compounds include additional components responsive to environmental conditions (pH, ionic strength, temperature), receptors for molecular recognition, groups capable of pH buffering and groups capable of other substantial modifications to a cell culture medium.

Some embodiments of the present disclosure feature the use of solvents in reaction mixes of the present disclosure. Solvents may be used in order to dissolve precursors, linkers and/or cross-linkers of the present disclosure. In some embodiments, solvents are included in reaction mixes of the present disclosure in order to alter the rate of polymerization in the reaction (e.g, the dilution effect). In preferred embodiments, one or more solvents are added to a reaction mix of the present disclosure in order to reduce the density of precursors and linkers/cross-linkers in the reaction mix, thereby reducing the rate at which polymerization and the creation of a polymer network takes place.

Solvents may also be used to reduce entanglement density in the networks being formed, resulting in potentially favorable alterations in mechanical properties (e.g., superelasticity) and enhanced swellability as well as increases in effective mesh size.

Some embodiment of the present disclosure may be performed without the use of a solvent, or in the absence of a solvent.

Post-Polymerization Treatments and Loading

In particular embodiments of the present disclosure, following gel formation, the solvogel is dried, loaded with the agent to be delivered via immersion in a concentrated solution of that reagent, dried once more and made ready for application. In other embodiments, the polymer hydrogel may be stored wet. In some embodiments, a solvogel of the present disclosure is swollen in water or an aqueous solution after the first drying step and before loading, in order to extract residues not removed by the drying step. It should be noted that a number of variations in these steps are possible in order to vary the properties of the hydrogels. In particular, the loading and extraction steps may be combined, such that release of any residual unreacted components occurs in tandem with uptake of the species (one or multiple in one or multiple loading steps) to be incorporated into the gel; in fact, loading steps typically involve some extraction, with extractables usually remaining in the gel. Likewise, the species to be incorporated into the gel in certain embodiments may also be added to the initial reaction mixture and encapsulated directly. Reversible absorption and release of species present in the environment (carbon dioxide for instance) is also possible in some embodiments, and in some embodiments the release profiles and kinetics of these materials may be further engineered by adjusting loading times or performing intentional leaching steps following loading in order to induce the formation within the gels of gradients in the concentration of the material(s) to be released.

In preferred embodiments, a hydrogel of the present disclosure is prepared, washed, dried, sterilized and stored for later use. In some embodiments, before use, the hydrogel is placed in a solution containing the one or more agents to be delivered to a cell culture. The hydrogel will swell, taking up the solution as well as any agents it contains. In this way, a hydrogel of the present disclosure can be loaded with one or more compounds for delivery. The concentration of a compound in a hydrogel may be uniform throughout the gel or may not be uniform. Concentration profiles and/or gradients within the gel can be controlled by varying the size and shape of the gel, the concentration of the agent in the solution, and the time of exposure of the hydrogel to the agent in solution. Concentration gradients may also be created with a hydrogel of the present disclosure by partial immersion of the hydrogel in a solution. Concentration profiles and/or gradients can also be manipulated by intentional leaching of the agent from the gel after loading. In some embodiments, the hydrogel is dried after loading and stored for use at a later date. In some embodiments, the hydrogel is sterilized before, after or both before and after loading of the gel. In some embodiments, the washing and loading steps of hydrogel preparation may be combined.

In some embodiments of the present disclosure, the reaction mixtures used to make hydrogels are formulated to include agents that are not involved in the polymerization of the precursors, in order to incorporate these agents into the gels. In some embodiments, these agents can be nutrients, cell media modifying agents or compounds that serve to indicate one or more conditions within the culture.

As an example of loading, in one embodiment of the present disclosure, a pH-sensitive hydrogel that swells in response to falling media pH is formulated to incorporate glucose, a base or buffer for raising the pH of cell culture media and any additional agents, nutrients or compounds. When used in a culture of cells, the hydrogel will react to cellular consumption of glucose and cellular production of lactic acid (and the concomitant reduction in pH) by swelling and thereby releasing glucose, base and any other compound that the user has chosen to incorporate into the gel. The base serves to counteract the production of lactic acid, the reduction in media pH and the swelling of the hydrogel itself. In this way, loading allows a pH-sensitive hydrogel that swells in response to acidic conditions to be self-regulating, through the loading of a basic compound that will counteract the swelling caused by the acidification of the media. In this case, loading also permits delivery of compounds to cell culture media in response to cell growth and increased metabolism. In some embodiments, these compounds replenish the media, providing additional amounts of compounds found in fresh media that have been consumed by cultured cells.

In some embodiments of the present disclosure, hydrogels are prepared and then preserved through sterilization and/or desiccation of the gel. Hydrogels may be loaded before or after sterilization and/or desiccation. Hydrogels that have some water, aqueous solution and/or solvent removed or that have essentially all liquid removed may be stored for use at a later time; such hydrogels may be reconstituted with the addition of water or cell culture media to the hydrogel. Some hydrogels may be sterilized by the use of high temperature and pressure (e.g., with an autoclave) or may be preserved or sterilized through other processes, such as irradiation.

Preferred Embodiments of Hydrogel Formation
Epoxy-Amine Cross-Linking

In a preferred embodiment, hydrogels of the present disclosure employing epoxy-amine cross-linking can be created by reacting a combination of epoxy and amine functional precursors such that at least some species comprise the minimum average number of functional groups required to induce cross-linking. The desired pH sensitivity is achieved, in part, though the use of amine-functional precursors. The amine groups on the amine-functional precursors remain pH sensitive following the hydrogel formation (e.g., cross-linking reaction). The use of amine functional precursors maximizes the number of pH-responsive groups in the hydrogel. The greater the concentration of pH-responsive groups (e.g., amines) present in the hydrogel, the greater its capacity to absorb acidic metabolites and the more pH-sensitive its swelling behavior becomes.

The amine functional precursor may be a small molecule or a macromolecule, such as amine functional polyethers, polyimines or polysiloxanes. It may be linear and branched. In a preferred embodiment, the amine functional precursor may be selected from any amine-containing compound disclosed in the present disclosure as well as the group consisting of amine-terminated poly(ethylene oxide), poly(ethylene glycol), poly(propylene oxide), poly(propylene oxide-block-ethylene oxide-block-propylene oxide), poly(tetramethylene oxide) poly(dimethylsiloxane) and poly(ethyleneimine) oligomers/macromolecules/polymers. The term "amine-terminated" comprises terminal amines at the terminus of the precursors as well as those pendant thereto, or substituted on, the precursor. An amine functional precursor with pendant amine functionalities rather than amines at the terminus of chains or branches may also be selected, for example poly(dimethyl-co-aminopropylmethylsiloxane).

Preferably, the amine functional precursor comprises at least two amine hydrogens. In some embodiments, the amine functional precursor comprises at least two, three or four amine hydrogens. In preferred embodiments, the amine functional precursor is 1,4-bis(3-aminopropyl)piperazine:

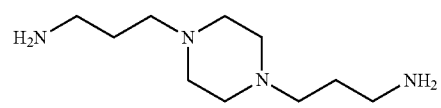 [SMILES: NCCCN1CCN(CCCN)CC1]

Jeffamine® ED-600, Jeffamine® ED-900, Jeffamine® ED-2003, Jeffamine® EDR-148, Jeffamine® EDR-176, poly(ethyleneimine) average molecular weight between about 500 and about 10,000 Da, preferably about 600, about 1,200 or about 1,800 Da, Jeffamine® T-3000, Jeffamine® T-5000, Jeffamine® XTJ-542, Jeffamine® XTJ-559, homopiperazine, 1-(2-aminoethyl)piperazine, polyetheramines, or mixtures thereof.

The epoxy-amine hydrogel networks may be formed by the reaction of epoxy groups with amine groups. In a preferred embodiment, the reaction involves epoxy groups and amine hydrogens. In one embodiment, a single primary amine ($NH_2R$) has a functionality of two (i.e., meaning two different epoxy groups may react the same amine group). The second epoxy-amine reaction at the same amine group proceeds in a comparable speed to the reaction of any other secondary amine in the system. In one embodiment, the precursor comprises a single primary amine. In other embodiments, the precursor is a pH buffer comprising a single (primary) amine group. The pH buffer may be selected from any pH buffer commonly used in cell cultures and able to form an epoxy-amine hydrogel network of the present disclosure.

The epoxy functional linker/cross-linker may be selected from any molecule comprising at least two epoxy functional groups. Preferably, epoxy functional linker/cross-linker may be selected from any molecule comprising at least three epoxy functional groups, at least four epoxy functional groups, at least five epoxy functional groups, or at least six epoxy functional groups. The epoxy functional compound may be a polyol glycidyl ether, an aliphatic polyepoxide, a cycloaliphatic polyepoxide, an aromatic polyepoxide, an alkoxylated polyol glycidyl ether or mixtures thereof.

In a preferred embodiment, the epoxy functional linker/cross-linker may be selected from any epoxy-containing compound disclosed in the present disclosure as well as trimethylolpropane triglycidyl ether (TMP-TGE):

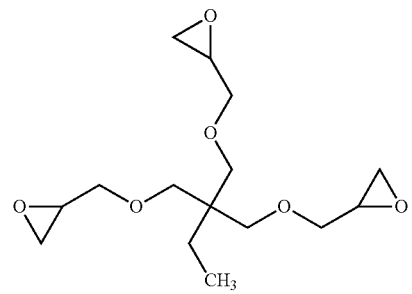 [SMILES: CCC(COCC1CO1)(COCC1CO1)COCC1CO1]

glycerol triglycidyl ether (G-TGE):

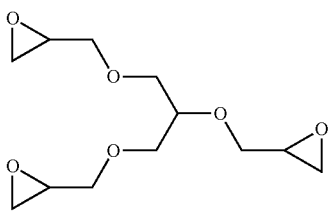 [SMILES: C(OCC1CO1)C(COCC1CO1)OCC1CO1]

propoxylated glycerol triglycidyl ether (PPG-TGE):

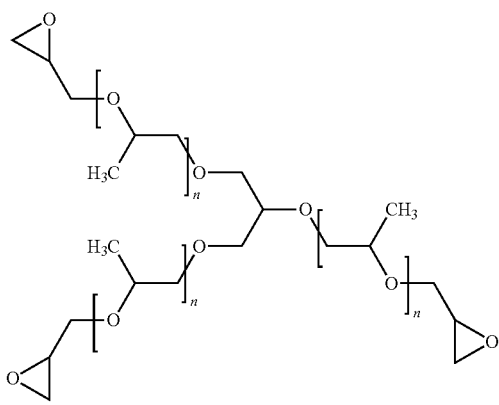

wherein n is 0 to 50; poly(glycidyl methacrylate) or its copolymers, sorbitol hexaglycidyl ether (S-HGE):

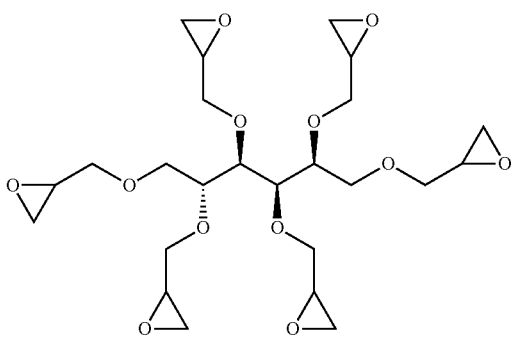 [SMILES: C(OC[C@H](OCC1CO1)[C@@H](OCC1CO1)[C@H](OCC1CO1)[C@@H](COCC1CO1)OCC1CO1)C1CO1]

Heloxy® 48, PEG-DGE, Erisys® GE-36, Erisys® GE-60, and glycidyl glycerol ether. Trimethylol propane, trimethylol ethane, glycerol, sorbitol and other sugar alcohols may be interchangeable cores for the polyepoxides. These materials may also be alkoxylated.

In one embodiment, the present disclosure relates to a pH-responsive hydrogel polymer corresponding to formula (I):

$$[A]_{(m+2)}[P]_x\text{-}[L]_y[E]_{(n+2)} \qquad (I)$$

wherein P is a pH-sensitive precursor or mixture of pH-sensitive precursors, L is a linker or mixture of linkers, A is an amine hydrogen, and E is an epoxy group. The variables x and y may relate to molecular weight, mass fraction or weight percent of the components. The pH-sensitive precursor and the linker are covalently attached to each other in the polymer hydrogel. The pH-sensitive precursor may comprise an average functionality of more than two amine hydrogens per molecule when the linker comprises an average functionality of at least two epoxy groups per molecule. Alternatively, the pH-sensitive precursor may comprise an average functionality of at least two amine hydrogens per molecule when the linker comprises an average functionality of more than two epoxy groups per molecule. In other embodiments, the sum of m+n is greater than zero.

The molecular weight and the functionality of each component, e.g. pH-sensitive precursors or linkers, are related. A component having a high functionality may be used with a high molecular weight component. A component (or the average of different components, such as two different pH-sensitive precursors) having a high functionality and too low a molecular weight may result in a hydrogel having a high crosslink density. The polymer hydrogel of the present disclosure may comprise a component(s) having an average reactive group concentration per unit mass (or volume, if appropriate) between about 0.1 and about 50 meq/g.

The pH-sensitive precursor, or group of pH-sensitive precursors, may have an average reactive group concentration per unit mass between about 0.5 and about 50 meq/g, preferably between about 1.0 and about 30 meq/g. The linker, or group of linkers, may have an average reactive group concentration per unit mass between about 0.5 and about 30 meq/g, and preferably about 1.0 and about 10 meq/g.

In one embodiment, the hydrogel polymer of the present disclosure comprises a pH-sensitive precursor having an average reactive group concentration of between about 0.5 and about 50 meq/g, preferably about 1.0 and about 30 meq/g, and a linker having an average reactive group concentration of between about 0.5 and about 30 meq/g, preferably about 1.0 and about 10 meq/g.

The polymer hydrogel of the present disclosure may have a mass fraction of pH-sensitive precursor(s) between about 0.05 and about 0.85. The polymer hydrogel of the present disclosure may have a mass fraction of linker(s) between about 0.15 and about 0.95.

The polymer hydrogel of the present disclosure may have an acid absorption capacity (e.g., amine group content) of between about 0.1 and about 10 meq/g in either the dry or wet state. Preferably, in a dry state, the polymer hydrogel may have an acid absorption capacity between about 0.4 and about 6.0 meq/g. Preferably, in a wet state, the polymer hydrogel may have an acid absorption capacity of about 0.1 to about 4.0 meq/g. For the wet state, the acid absorption capacity is preferably measured at equilibrium swelling wherein few of the amines should be protonated. In some applications, the difference in swelling between the acidified and the non-acidified portions of the material should not be so great as to cause the network to rupture, for example under more extreme conditions like swelling at pH 2.

In a preferred embodiment, at least one of the reagents used to form the epoxy-amine based network (e.g., epoxy linker/cross-linker and/or precursor) is a liquid at room temperature or a solid at room temperature with a melting point close to room temperature. A melting point close to room temperature is one that facilitates mixing. In other embodiments, a mixture of the precursor and the linker/cross-linker is a liquid at a temperature below 100° C., preferably below 80° C., and more preferably below 60° C. In some embodiments, the systems will start to crosslink if the temperature is too high in attempting to mix them, making mixing at too high of a temperature impractical. Preferably, the mixture of all components of interest is liquefied at a temperature not so high as to preclude complete mixing due to network formation and/or thermal degradation.

In some embodiments, the mixture of epoxy and amine functional precursors (i.e. epoxy linker/cross-linker and precursor) exhibits no phase-separation between components at any point during processing, e.g., there is no polymerization-induced phase separation. The mixture is homogenous to ensure uniform properties in the final material.

In a preferred embodiment, the epoxy-amine network may be formed in the absence of a solvent. The absence of a solvent reduces costs and decreases the time it takes to form the hydrogel network. In some embodiments, the reaction time to form the hydrogel is under 4 hours, preferably under 2 hours, more preferably under 1 hour. In other embodiments, the reaction time is under 45 minutes, preferably under 30 minutes and more preferably under 15 minutes.

Moreover, in the absence of a solvent, the hydrogel experiences limited or no shrinkage typically associated with the removal of solvent from hydrogels formed using a solvent. It is also known that epoxy resins adhere to a wide range of surfaces, especially polar ones (i.e. glass, ceramics, metals, and plastics). By limiting shrinkage, an epoxy based hydrogel of the present disclosure formed in the absence of solvent may be applied as functional coatings in addition to free-standing beads, pellets monoliths, etc.

In solvent based hydrogel systems, a hydrogel applied to a substrate is swollen with solvent and must undergo substantial volume change when the solvent is removed. Upon solvent removal, the hydrogel shrinks and the bonded hydrogel is subject to large shear forces as the film attempts to shrink in all directions (including laterally), making peel-off likely. In contrast, when solvent-free systems cure there will be a very slight reduction in volume. As a result, film stresses will be negligible and peel-off will not occur. When the solvent-free system is subsequently swollen in water, stress may occur at the interface between the film and the substrate. Since the hydrogels can be tuned in regard to swellability, however, it is possible to make a functional coating that does not significantly swell, meaning the stresses would be not too high and it would not peel off.

In some embodiments, the hydrogels of the present disclosure may form composite hydrogel coatings. For instance, one epoxy-amine hydrogel may be prepared on a substrate. Thereafter, a second epoxy-amine hydrogel may be prepared on the same substrate to form a core-shell composite structure. Such a composite is difficult to achieve in a solvent based system because the solvent used to deliver the second hydrogel material will likely swell the original, dry, hydrogel or not shrink to the same extent as the wet core.

In another embodiment, the hydrogel networks of the present disclosure may allow for additional metrics to be used to predict the hydrogel behavior. For a given hydrogel composition, the amount of swelling at high pH (e.g., 9, where the hydrogel may be uncharged) and the amount of swelling at low pH (e.g., 2, where the hydrogel may be completely charged and swell more) may be measured. The difference between the two may give an indication of the degree of pH sensitivity the hydrogel will exhibit, for example, in regard to release behavior. Hydrogels of difference pH sensitivity, as measured herein, may be formed by select combination of different materials.

In addition to using starting materials of reduced or minimal toxicity, preferred hydrogels of the present disclosure swell in water and do so without causing any measurable pH changes in the water. In some embodiments of the present disclosure, the precursors are water soluble and extremely alkaline; even small quantities of free, unreacted precursor extracted from the gels and dissolved in the water would substantially increase its pH. Thus the lack of substantial change in pH upon swelling suggests that the polymerization reaction in this embodiment is substantially complete, which in turn indicates that the hydrogels pose little or no risk of leaching toxic residues into cell media. Preferred embodiments of the present disclosure feature starting materials that have advantageous properties, such as the ability to react substantially completely with other components in the reaction mix, and substantially reduced or minimal inherent toxicity to cell culture cells.

Properties of Hydrogels

Hydrogels of the present disclosure can be formulated to provide a wide range of properties. Variations in formulation can create a variety of hydrogels, differing in swellability, amount of environmental sensitive (including none), distance between links and cross-links (thereby altering the mesh size of the gel matrix), as well as the physical and mechanical properties of the hydrogels. Arbitrary variations in composition are possible with little or no change in processing procedures.

In some embodiments, hydrogels prepared with synthetic precursors feature minimal biodegradability and lack of dissolvability or degradability in aqueous solutions or water. In some embodiments, hydrogels of the present disclosure provide polymer networks with polymer chains and junction points, links or cross-links between the chains that secure the polymer chains into a network configuration and prevent the chains from dissolving under any circumstances. In preferred embodiments, hydrogels of the present disclosure feature advantageous properties such as low cytotoxicity, high mechanical strength, ability to be sterilized, ability to deliver compounds to a media, ability to scavenge compounds from a media and resistance to degradation.

A preferred embodiment of the present disclosure features a hydrogel comprised of a biocompatible, inexpensive, pH-sensitive polymer network, created with readily-available, off-the-shelf commercial ingredients that have consistent purity and properties and can repeatedly be used to create hydrogels of consistent high quality, homogeneity and uniformity.

In some embodiments, the extractable/soluble fraction is mainly polymeric in character, due to the fact that a higher mass of precursor is needed than of cross-linker in order to maintain reaction stoichiometry (even in these cases, however, the formula can be easily optimized so as to minimize the extractable fraction). This is relevant to the issue of toxicity in that precursors can be chosen that have good records of safety in biomedical applications.

Sterilizable Hydrogels

Hydrogels of the present disclosure feature sufficient stability for a range of sterilization techniques. In some embodiments, hydrogels of the present disclosure survive autoclaving at 120° C. and 2 atm with no mass loss or color change. The hydrogels of the present disclosure have the additional advantages of excellent thermal stability as well as good stability.

Hydrogel Mechanical Strength

In terms of mechanical stability, tests on some embodiments of the present disclosure comprising pH-responsive gels have revealed very high toughness and tolerance to strain, consistent with the so-called "superelastic" behavior of polymer networks having very low entanglement densities. Hydrogels prepared in solvent show this behavior to a greater extent than solvent-free systems. In a preferred embodiment, hydrogels have a stiffness that is intermediate between that of a rigid thermoset (e.g., epoxy resin) and that of a soft rubber (e.g., silicone). For example, one embodiment of the present disclosure, H-600, shows a modulus of ~4.5 Mpa in the dry state (measured using DMA). In some embodiments of the present disclosure, the stiffness of the pH-responsive hydrogel materials is sufficiently high that they are unlikely to warp or deform during vigorous agitation in solution, even in the swollen state, but that they are not so rigid in the dry state that they are subject to handling-induced cracking or fracture. With these properties, embodiments of the present disclosure feature robust and practical-to-use hydrogel materials whose release behavior will not change as the result of handling or vigorous stirring of the medium in which they are placed.

Mesh Size, Swellability and Responsiveness of Hydrogels

A wide variety of mesh sizes can be selected for hydrogels of the present disclosure by altering the length of the precursors, since in a preferred method of the present disclosure the reaction that creates the precursor bridge between adjacent cross-links will consist of exactly one precursor chain. Likewise, in some methods of the present disclosure, each crosslink will connect to three and only three precursor chains, which allows the construction of a very accurate picture of a wide variety of networks based simply on the choice of components and greatly enhancing the ability to control the properties of these networks as a result.

In some embodiments, hydrogels can be formulated to respond to environmental changes with changes in their content of water or aqueous solution. In particular, the swelling-deswelling behavior of polymer networks with respect to the environmental pH can be characterized and correlated to network morphology (mesh size and cross-linker structure). Swelling behavior, independent of the nature of the stimuli, can be generalized through mechanical testing. With methods of the present disclosure, the relationships between gel morphology and swelling behavior can be predicted, and the behavior of a particular network can be more readily predicted. Additional advantages of the systems and materials featured in some embodiments of the present disclosure include the ability to incorporate one or more dyes to sense multiple environmental conditions, from pH to ion concentration to swelling and deswelling.

To create responsive, environmentally sensitive hydrogels, hydrogels of the present disclosure can be formulated with polymers or polymeric side chains that will react to changes in cell culture media. As mentioned above, hydrogels of the present disclosure can be formulated with particular polymers that will lead to swelling of the hydrogel in response to changes in the pH of cell culture media. In particular embodiments, some hydrogels with basic side-chain residues will swell in response to acidic conditions and thereby become more permeable to agents within the gel matrix and to compounds in the media. This increase in permeability can lead to an induction of compound release or absorption or an increase in the rate of compound release or absorption to or from the hydrogel. In some embodiments, hydrogels can be created that are sensitive to changes in temperature. These hydrogels are created with polymers whose solubility is due primarily to weak and easily disrupted hydrogen bonds with water. Above a certain critical temperature, these hydrogen bonds are disrupted and the polymers become insoluble or less soluble, leading to reduced swelling of the gel.

Preferred embodiments of the present disclosure feature hydrogels that react to changes in cell culture media pH levels by swelling or by deswelling, depending on the direction of the change (from higher pH to lower, or vice versa). In some embodiments, the range and breadth of the pH sensitivity of a hydrogel can be altered with changes in the component precursors and/or cross-linkers, changes in the formulation of the reaction mix used to form the gel, and/or changes in the gel forming or post-production treatment protocols.

Hydrogel Variations

The properties of hydrogels are dependent upon multiple factors, including the ingredients chosen for incorporation, the formulation, the solvent(s) used and any post-polymerization treatments or procedures. Through alterations to these and other variables, hydrogels can be designed to have particular properties needed for specific uses.

In some embodiments of the present disclosure, a polymerization initiator or agent is added to initiate polymerization or alter the rate of polymerization. If pores are desired, a porogen (e.g., sodium chloride, ice crystals, and sucrose) may be incorporated into the liquid reaction mixture. Pores may also be created via reaction-induced phase separation. In this technique, with the selection of a solvent with the appropriate properties, the polymer network will phase-separate from the solvent at some point following the initiation of gelation but prior to the completion of the network. Thermally-induced phase separation is also possible with some embodiments of the present disclosure, where changes in the reaction mix temperature are sufficient to cause phase-separation with a solvent and create porosity. An additional technique to create porosity in some embodiments is the use of freeze-thawing to create temporary solid crystals of a solvent. One with skill in the art would recognize that multiple porosity-generating techniques are compatible with embodiments of the present disclosure, including supercritical drying (useful for creating substantially smaller pores, i.e. micropores); gelation in a microemulsion; microemulsion synthesis that creates a suspension of discrete hydrogel particles which are then glued together to form a "string-of-pearls" type porous body; physical and chemical foaming; and other techniques.

In some embodiments of the present disclosure, a solvent will also be used to dissolve solid monomer(s) and/or polymers to create ingredient solutions for the polymerization reaction. However, in some embodiments of the present disclosure, for example in cases where only liquid monomers are used, there may be no need for inclusion of a solvent.

One with skill in the art would appreciate that hydrogels of the present disclosure can be created with a wide variety of properties and could incorporate a wide variety of agents, so that some hydrogels of the present disclosure could be created for use with a particular cell type, to maintain a particular range of cell culture conditions or to deliver particular compounds or molecules.

Selection of Polymer, Cross-Linker and Solvent

Some physical properties of hydrogels of the present disclosure can be adjusted by varying parameters such as the solvent used, the concentration of precursors(s), the concentration of cross-linker and the conditions under which polymerization takes place. Additional compounds may be added to modify the polymerization process and thereby modify physical attributes of the hydrogels. In some embodiments, the stability of the physical properties of the produced polymer hydrogel can be enhanced by controlling the amount of covalent cross-links. By altering the selection and concentration of precursors, cross-linkers and solvents, physical properties such as the amount of water or aqueous solution hydrogels hold when in a swollen state, the average mass of the polymer(s) that comprise the chains of the network or matrix and the mesh size of the network can be altered.

Hydrogels of the present disclosure may feature low production cost via the use of off-the-shelf synthetic polymer solutions that provide for consistent purity, consistent and predictable reactivity in gel formation reactions, complete reactivity that consumes all available precursor, consistent hydrogel performance and low hydrogel toxicity.

Compound Incorporation and Loading

Hydrogels of the present disclosure may be designed or formulated to deliver compositions into an aqueous solution or cell culture media. Hydrogels of the present disclosure may also be designed or formulated to comprise compositions that provide some useful functionality to the hydrogel. Some formulations include additional compounds or agents not required for the creation of the hydrogel into the solution(s) of polymer(s) used to create the hydrogels. Thus some hydrogels of the present disclosure are synthesized from compositions incorporating a compound not required for hydrogel formation along with an acceptable polymer for the creation of a polymer network. A compound incorporated into a hydrogel of the present disclosure may be associated with the hydrogel through a chemical bond (covalent or ionic) and may be incorporated via physical encapsulation by the polymer network.

By various procedures, hydrogels can be created that incorporate compositions into the hydrogel. Some hydrogel designs permit the introduction of compounds into the hydrogel after the hydrogel network has formed. In some hydrogels of the present disclosure, compounds are included in or loaded into the hydrogel in order to be released into an aqueous solution or cell culture media at a later time. This release may be spontaneous, continual and/or in reaction to a change in the hydrogel or in the aqueous solution or cell culture media into which the hydrogel has been introduced. The release may end at a later time and the ending of the release may be in reaction to a change in the hydrogel or in the aqueous solution or cell culture media into which the hydrogel has been introduced.

Hydrogels of the present disclosure may provide for compositions for sustained delivery of an agent in a controlled fashion. The composition can retain the agent and prevent the agent from being used, consumed or affecting cells in a culture, until a response from the composition releases or deprotects the agent. Compositions of the present disclosure can incorporate a wide variety of organic solvents with solubility ranging from high water solubility to low water solubility. A wide variety of agents can be incorporated into compositions of the present disclosure. Examples of suitable agents include substances required by a cell in the culture for growth or production of a molecule or compound by the cell; compounds that induce a change in a cell in culture (e.g., change the metabolism or genetic expression of a cell in culture), including compounds that augment a function of a cell or create a change in the differentiation of a cell in culture; compounds that condition the media, including compounds that create media conditions that are more favorable for cell growth and survival and compounds that have been depleted in the cell culture media; compounds that reduce the risk of contamination of the cell culture, including antimicrobial agents such as antibiotic, antiviral and antifungal agents; antimicrobial agents that may be introduced to study their effects on cells or on microbes or to modulate the activity of microbes that were introduced into the culture deliberately or inadvertently; compounds that create media conditions that are conducive to the preservation of compounds or molecules found in the cell culture and/or produced by a cell in culture; compounds that serve to bind or sequester target compound(s) in the media or produced by cells; compounds that can serve to signal information about the culture to an observer or a device outside of the culture, including environmentally sensitive dyes or dye-labeled particles and including agents that remain embedded in the hydrogel when used and agents that are released into the cell culture media; compounds that change the properties of the hydrogel after its formulation, including compounds that alter the rate of release or absorbance of compounds to or from the media and compounds the change the responsiveness of the hydrogel to conditions in the cell culture media; compounds that are the subject of experimentation; and compounds whose effect on a cell in culture is unknown. Other agents that may be used with compositions of the present disclosure include microparticles, nanoparticles or oligomeric molecules such as peptides and nucleic acids. Those with skill in the art would be able to design a formulation of a hydrogel of the present disclosure and protocols for their preparation and use that would allow the incorporation and release of a particular agent from the hydrogel. Some nanoparticles and microparticles for use with hydrogels of the present disclosure serve to protect an agent for a required period of time from exposure to organic solvents or other materials found in composition mixtures, the polymer network or cell culture media. Formulas for the formation of hydrogels or the treatment of hydrogels after formation can include mixtures or solutions comprising other components such as emulsifying agents, surfactants, excipients, colorants and the like to stabilize or alter the hydrogel, the agents that may be incorporated into the hydrogel or the aqueous solution or media into which the hydrogel is or will be placed. In some embodiments of the present disclosure, oriented, high-aspect-ratio particles may be included and aligned (via mechanical/shear, electrical or magnetic fields) in such a way as to give directional release characteristics (e.g., higher or lower rates of release or scavenging on a particular face or from a particular portion of the hydrogel) or may add functionality (e.g., additional absorption capacity).

Some embodiments feature the inclusion of one or more compositions that can sense the environmental conditions of the medium into which the hydrogel has been placed. In preferred embodiments, one or more of these compounds can be pH-sensitive dyes, ion concentration-sensitive dyes, dyes that can sense the swelling and/or the deswelling of the hydrogel, or particles tagged with any of these dye types.

Porous Hydrogels

Hydrogels of the present disclosure include hydrogels without pores and hydrogels with a variety of pore sizes. For example, a swellable hydrogel of the present disclosure which expands when acted upon by a given stimulus is to be synthesized by solution polymerization and cross-linking. In order to generate a porous structure for the hydrogel, polymerization may be carried out in a solvent which dissolves the prepolymer(s) and (cross)linker(s) but is not a solvent for the crosslinked network. The resulting crosslinked networks have a porous structure. However, the detailed synthetic conditions and procedures for the manufacturing of the (porous) hydrogel may depend upon monomer and polymer properties. Some hydrogels of the present disclosure have no appreciable pores in their structures. A wide variety of techniques exist and additional techniques may be developed for imparting porosity to hydrogels of the present disclosure.

A hydrogel with a porous structure can be created through the incorporation of a porogenic agent. Porosity is formed by the subsequent removal of the porogen from the resultant solid hydrogel (e.g., by repeated washing). In some embodiments of the present disclosure, the porosity of the hydrogel material is imparted due to a supersaturated suspension of a porogen in the precursor solution. A porogen that is not soluble in the precursor solution, but is soluble in the washing solution can also be used. A variety of porogens can be used in the formation of hydrogels of the present disclosure, including sodium chloride, potassium chloride, ice, sucrose, and sodium bicarbonate. In some embodiments, it is preferred to control the particle size of the porogen to less than 25 microns, more preferably less than 10 microns. The small particle sizes aid the suspension of the porogen in the solvent. Preferred concentrations of the porogen range from 5% w/w to 50% w/w, more preferably 10% w/w to 20% w/w, in the precursor solution. Alternatively, the porogen can omitted and a non-porous hydrogel can be fabricated. In some embodiments of the present disclosure, the inclusion of a porogen serves to increase the surface area of the hydrogel.

Automatic Compound Exchange

Hydrogels of the present disclosure may be designed to deliver a compound, a molecule and/or an ion to an aqueous solution or to cell culture media when placed in the solution or media. Hydrogels of the present disclosure may be designed to absorb or scavenge compounds, molecules or ions from a cell culture media when placed in the solution or media. Such designs may allow for continual release and/or scavenging of the compound, molecule and/or ion into and/or from the solution or media over time. Some hydrogels will respond to changes in the conditions of a solution or media with changes in the rate of release or absorbance of a compound to or from the solution or media. Hydrogels of the present disclosure can provide delivery or absorbance of compounds to or from a solution or media without human intervention or manipulation of the solution or cell culture. In this way, some hydrogels can reduce the risk of cell culture contamination by reducing the amount of intervention or manipulation of the media by personnel required to maintain the cell culture. Some hydrogels may be used to create more optimal conditions and/or higher productivity in a cell culture by providing a more frequent addition or withdrawal of compounds from media than is feasible to obtain through manual intervention or manipulation of cell cultures by personnel. By releasing or absorbing compounds or molecules into or from cell culture media, some hydrogels of the present disclosure serve to reduce the overall cost of cell culture by reducing the amount of labor required to maintain cell cultures.

In a preferred embodiment of the present disclosure, one or more commercially available, off-the-shelf precursor component(s) may be selected that are (in and of themselves, or contain moieties or side groups that are) sensitive to changes in pH. In particular, these polymers may become more soluble at a pH reading that corresponds to the normal acidification of cell culture media during the course of cell growth in a culture. These polymers may be combined with cross-linkers to form a polymer network. A solvent, including water, may be used in the network formation reaction. Alternatively, the formation of the network may occur in the absence of a solvent. The solvogel product then has the constituent liquid or solvent removed to form a xerogel product. The product is a chemically stable, physically robust and autoclavable solid that can be loaded with a variety of agents and/or modified to provide a range of desired functionalities. In some embodiments of the present disclosure, the products are formulated to include agents that are not involved in the polymerization of the precursors. In some embodiments, these agents can be nutrients, cell media modifying agents or compounds that serve to indicate one or more conditions within the culture. In a preferred embodiment, one of the compounds that serves to indicate a condition within the culture is a pH-sensitive dye. In some embodiments, the one or more compounds that serve to indicate one or more conditions within the culture can be retained in the hydrogel or can be released into the cell culture media. The one or more compounds serving to indicate one or more conditions in the cell culture media can be bound to the polymer network through covalent, ionic or hydrogen bonding and/or are retained due to the molecular size(s) of the compound(s) and the mesh size of the polymer network.

A pH-sensitive hydrogel, as described in embodiments of the present disclosure, that swells in response to falling media pH is formulated to incorporate glucose and/or L-glutamine or its derivatives as well as a base for use in maintaining the pH of cell culture media as it drops during cell metabolism, and any additional agents, nutrients or compounds. When used in a culture of cells, the hydrogel will react to cellular consumption of glucose and cellular production of lactic acid (and the concomitant reduction in pH) by swelling and thereby releasing glucose (and/or L-glutamine or its derivatives) and base and becoming permeable to lactic acid. Glucose levels and pH will rise and lactic acid levels will also be reduced as the lactic acid diffuses into the hydrogel. A rise in pH level from the release of base into the media serves to deswell the hydrogel and reduce permeability and release of compounds into the media. In this way, this hydrogel has an autoregulatory function and can serve as a glucose (and/or L-glutamine) and base reservoir (as well as a reservoir for other nutrients and agents) for an extended period of time. In some embodiments, a hydrogel of the present disclosure is capable of maintaining D-glucose concentrations above or approximately 3.0 g/L or 4.0 g/L for 24 to 72 (e.g., for 24 to 48) hours post-culture seeding without any replacement of the cell culture media. In some embodiments, a hydrogel of the present disclosure is capable of maintaining D-glucose concentrations of approximately 3.0 g/L to 4.0 g/L for 24 to 72 (e.g., for 24 to 48) hours or more post-culture seeding without any replacement of the cell culture media. In preferred embodiments, hydrogels of the present disclosure are formulated to release glucose into a cell culture media so that D-glucose concentrations are maintained within a range between approximately 4.0 and 5.5 g/L (e.g., between approximately 4.0 and 4.5 g/L) for a period of two to ten days, more preferably approximately one week. Embodiments of the present disclosure feature hydrogels that are formulated to release L-glutamine or its derivatives into cell culture media so that glutamine concentrations are maintained between approximately 0.5 mM and 10.0 mM. In preferred embodiments, hydrogels of the present disclosure are formulated to release L-glutamine or its derivatives into cell culture media so that glutamine concentrations are maintained between approximately 2.0 and 4.0 mM for a period of two to ten days, more preferably approximately one week. Hydrogels of the present disclosure comprise hydrogels capable of maintaining minimum D-glucose levels for extended periods of time of approximately 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.00, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.00, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, 8.45, 8.50, 8.55, 8.60, 8.65, 8.70, 8.75, 8.80, 8.85, 8.90, 8.95, 9.00, 9.05, 9.10, 9.15, 9.20, 9.25, 9.30, 9.35, 9.40, 9.45, 9.50, 9.55, 9.60, 9.65, 9.70, 9.75, 9.80, 9.85, 9.90, 9.95 and 10.00 g/L. Hydrogels of the present disclosure comprise hydrogels capable of maintaining minimum L-glutamine levels for extended periods of time of approximately 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.00, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.00, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, 8.45, 8.50, 8.55, 8.60, 8.65, 8.70, 8.75, 8.80, 8.85, 8.90, 8.95, 9.00, 9.05, 9.10, 9.15, 9.20, 9.25, 9.30, 9.35, 9.40, 9.45, 9.50, 9.55, 9.60, 9.65, 9.70, 9.75, 9.80, 9.85, 9.90, 9.95 and 10.00 mM.

Hydrogels of this present disclosure can react automatically to changes in cell culture media without human intervention and can do so at any time, thereby allowing treatment, restoration and/or maintenance of cell culture media during times when no lab personnel are present. The hydrogels can serve to address and adjust cell media conditions as they change and prevent larger changes from occurring, allowing for cell cultures that spend longer periods within optimal media parameters than is possible with a fully manual cell culture system. Through the maintenance of more optimal media parameters in cell cultures, use of hydrogels of the present disclosure can lead to higher yields of cell-synthesized compounds, higher rates of cell growth and survival and lower rates of contamination than would be possible under normal fully manual cell culture maintenance procedures.

Thus, in a preferred embodiment of the present disclosure, hydrogels serve as a non-mechanical, automated yet cost-effective nutrient incorporation system for cell culture. These hydrogels can be consistently and reproducibly manufactured using standard reagents and easily sterilized, preserved and stored. Properties of these hydrogels can be tweaked or altered to accommodate a wide range of cell culture needs through changes in the component polymers and cross-linkers, changes in the concentration or preparation of reaction mix solutions and/or changes in the gel formation or post-formation treatment protocols. By reducing the amount of manipulation by scientific personnel required by the cultures and the number of times cell culture containers need to be opened, hydrogels can reduce the risk of culture microbial contamination. Hydrogels of the present disclosure can serve to both improve cell culture conditions and the performance, production rates and survivability of cultured cells while simultaneously reducing labor requirements and costs of cell culture operations. In this way, hydrogels of the present disclosure increase the bioactivity of cell cultures, increase the longevity of cultured cells in small volumes, or increase productivity of individual cell cultures as well as entire cell culture operations and help lower the costs of running a cell culture facility.

In some embodiments of the present disclosure, the rates of release or scavenging of two or more compounds to or from a hydrogel will be substantially similar or can be substantially different. Hydrogels of the present disclosure comprise hydrogels designed with particular components or by particular processes in order to influence the rate of release or scavenging of a particular compound, molecule and/or ion to or from a cell culture media. For example, techniques described above can be used to generate porosity in a hydrogel of the present disclosure, with pores whose size falls within a desired set of parameters. By adjusting pores sizes, for example, one with skill in the art may increase the effective surface area of a hydrogel of the present disclosure for the release or absorbance of a particular compound, molecule and/or ion. In another example, changes in mesh size alter the rate of transport of one or more particular compounds, molecules and/or ions much more significantly than the rate of transport of one or more other particular compounds, molecules and/or ions through size exclusion.

Environmentally Reactive Hydrogels

The present disclosure also relates to compositions that release agents and/or drugs in response to environmental stimuli. In some embodiments, the compositions relate to delivery devices containing agent- or drug-laden hydrogels which swell or deswell and release agents or drugs from the device, either through diffusion, displacement or pressure (e.g. mechanical compression) in response to external or internal stimuli such as temperature or pH changes, or chemical reactions.

The present disclosure provides hydrogels that undergo controlled volumetric expansion or contraction in response to changes in their environment, such as changes in pH or temperature (i.e., they are "stimulus-expandable"). In some embodiments, the hydrogels of the present disclosure are prepared by forming a liquid reaction mixture that contains: a) monomer(s) and/or polymer(s) at least portion(s) of which are sensitive to environmental changes (e.g., changes in pH or temperature) and b) a cross-linker. In some embodiments, the polymerization reaction forming the gel matrix spontaneously occurs upon mixing of the components to form the reaction mixture.

A pH-sensitive hydrogel of the present disclosure may be reactive to pH values that are sub-optimally or abnormally lower or higher than the pH values of fresh or normal cell culture media. A pH-sensitive hydrogel of the present disclosure may swell or deswell in reaction to a change in pH. Hydrogels of the present disclosure include hydrogels that react to relatively acidic conditions but do not react to relatively basic conditions, hydrogels that react to relatively basic conditions but do not react to relatively acidic conditions, hydrogels that react in similar or different ways to both relatively acidic or relatively basic conditions, and hydrogels that do not appreciably react to changes in the pH of media.

Hydrogels of the present disclosure can be formulated to be sensitivity to a wide variety of different pH ranges. By altering the parameters of component selection and reaction conditions, one with skill in the art would be able to create pH-sensitive hydrogels of the present disclosure with sensitivity within pH ranges particularly useful for the culturing of particular cell lines. In a preferred embodiment, a hydrogel of the present disclosure is pH sensitive within a pH range of approximately 6.0 to 8.5 (e.g., between 6.2 and 8.2, between 6.5 and 8.0, or between 6.8 and 7.4). Additional preferred embodiments feature hydrogels capable of maintaining the pH value of a cell culture media between 6.8 and 7.2, and between 6.9 and 7.1, for an extended period of time. Additional preferred embodiments feature hydrogels capable of maintaining a pH value in a cell media close to 7.05, for example, a range of ±0.02 to ±0.05 pH value units from 7.05 for an extended period of time, e.g., beyond 36 hours from the seeding of a cell culture without a change of the media. In a more preferred embodiment, a hydrogel of the present disclosure with such a pH sensitivity range can maintain the pH of a cell culture media within 0.02 pH units of a preferred pH value of 7.05 for a period ranging from two days to ten days, more preferably for approximately one week. Additional embodiments feature hydrogels of the present disclosure that are reactive within a range of pH values spanning a pH value of approximately 6 to a pH value of approximately 8.5. Hydrogels of the present disclosure comprise hydrogels with a lower limit of pH responsiveness of 6.00, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, and 8.45. Hydrogels of the present disclosure comprise hydrogels with an upper limit of pH responsiveness of 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, 8.45 and 8.50.

In some embodiments of the present disclosure, substantially all of the precursor components of the present disclosure comprise pH-sensitive precursors. In some embodiments of the present disclosure, at least a portion of the precursors selected for inclusion in the formulation of a pH-sensitive hydrogel are pH-sensitive. Additional precursors may be added to provide additional mechanical properties (e.g., to impart additional compressive strength), to provide additional functionality to the hydrogel and/or to influence the process of polymer network formation.

Hydrogel Devices

Hydrogels of the present disclosure may be present in a commercial embodiment essentially as a singular component for use in a cell culture or may be incorporated into a device. A device into which a hydrogel of the present disclosure is incorporated may serve to protect the hydrogel during shipment or use, serve as a dispensing device, and/or may serve to regulate the activity of a hydrogel when used in a cell culture environment. Additional embodiments of the present disclosure include hydrogels produced for use with: specific types of cells; specific classes of cells; cells with particular modifications, including genetic modifications; cells of a specific species, organ or tissue of origin; cells for use in particular types of experimental environments or protocols; particular cell culture medias or types of medias, including medias containing any number of nutrient or compound variations; and/or particular cell culture media components or media systems. Additional embodiments of the present disclosure include hydrogels incorporated as parts of devices and as parts of kits for use in cell cultures or cell culturing systems.

Non-invasive Monitoring of Cell Culture Status

In some aspects, the cell culturing systems include means for non-invasive monitoring of the cellular environment within the system. The non-invasive devices, compositions, and methods of the present disclosure yield information from in vitro cell cultures for the assessment of intracellular and extracellular conditions within the cultures. In some embodiments, the devices, compositions and methods of the present disclosure can be used to monitor and determine pH levels or concentrations of nutrients, metabolites, compounds or agents within the cell culture or within the cells of the cell culture. Other embodiments of the present disclosure feature monitoring of other cell culture media parameters and the production levels, viability, growth rates and metabolic states of cultured cells. Embodiments of the present disclosure include methods of non-invasive measurement of the pH level of a cell culture, by providing a hydrogel with a pH-sensitive dye that allows visual or optical inspection of the hydrogel for changes in properties, e.g., color, indicative of changes in pH.

Truly non-invasive methods require that no device is placed into the cell culture vessel; that no probe is used to remove fluid or to inject materials into the cultures; and that the protective barriers of the cell culture vessel, such as the lids, caps or walls of a vessel, are not mechanically penetrated or otherwise physically compromised. In a preferred embodiment, a non-invasive monitoring device supplies continuous, accurate monitoring of any of a variety of cell culture parameters, including pH, nutrient concentration, product concentration, other extracellular states, and intracellular activity, such as cellular metabolic status. This can be done by monitoring the absorption or emittance of electromagnetic energy by reporter molecules in the cell culture, including reporter molecules embedded in a hydrogel or delivered to a culture by a hydrogel. In this way direct, real-time information regarding cell culture status is produced. In contrast, chemical sensors making periodic measurements of small portions of cell media removed from the culture provide less responsive, more indirect data regarding cell culture status while simultaneously raising contamination risk through contact with the cell culture media. Non-invasive methods also permit continual and real-time measurements of conditions within a cell culture.

As noted above, some embodiments feature hydrogels containing one or more compounds that serve to indicate one or more conditions within the culture. In these embodiments, the one or more compounds can be retained in the hydrogel or can be released into the cell culture media. In some embodiments, the one or more compounds serving to indicate one or more conditions in the cell culture media are bound to the polymer network through covalent, ionic or hydrogen bonding and/or are retained due to the molecular size(s) of the compound(s) and the mesh size of the polymer network.

Monitoring Via Optical Techniques

In preferred embodiments of the present disclosure, optical techniques can be used to monitor the hydrogel of the present disclosure including the incorporation of various probes (e.g., dyes, dye-tagged particles, quantum dots, etc.) and various measurement techniques (e.g., transmission, absorption, scattering, luminescence, fluorescence, phosphorescence, etc.). For examples, optical transmittance can be used to quantify any changes in the absorption spectrum of the environmentally sensitive dyes bonded to the hydrogels. While absorbance can be related directly to the concentration of the absorbing species via the Beer-Lambert Law, this approach can be limited by quenching due to dye-dye interactions and also interactions between the dye and the surroundings, as well as fluctuation of the light source and noise from the environment. With that in mind, the present disclosure provides for the use of the ratio of the absorbance at two wavelengths—one corresponding to the protonated (acidified) form of the dye and one corresponding to the non-protonated (non-acidified) form of the dye. With proper calibration, this ratio can in turn be directly correlated to a measurement of a condition or a reading for a particular cell culture parameter.

The present disclosure provides non-invasive sensor compositions that comprise one or more reporter molecules within the cell culture. Reporter molecules include reporters that are sensitive to conditions in the culture media, such as dye molecules that absorb discrete wavelengths of light depending upon conditions in the media, and varieties of small molecule metabolic reporters that can indicate the status of cultured cells. When contained within a cell culture, some reporters are able to interact with specific biologically active molecules in the media, on the surface of cells or within cells in such a way as to report the status of the media or the cultured cells while not interfering with cellular growth, production or metabolic function. The reporters provide a signal that can be used for multiple purposes including, but not limited to, assessment of metabolic function of cultured cells (e.g., as related to glucose metabolism and lactic acid production); monitoring of cell growth and survival; stress status of cells; determination of vitality and viability of cells based on metabolic function; measurement of constituent compounds of the cell culture media as well as compounds produced by cells, including waste products and products produced by cells intended for harvesting from the media. Specifically, applying the reporters of the present disclosure to hydrogels for delivery to cell cultures or directly to cell culture media can provide detailed information on the state of cell culture media as well as multiple metabolic pathways in cultured cells that can be analyzed by sight or by using automated devices or hand-held instrumentation.

As described above, hydrogels of the present disclosure may incorporate compounds that allow information about the status of the culture to be ascertained. In some embodiments, one or more compounds providing information about the status of a culture are incorporated into the hydrogel concurrently with formation of the hydrogel or at some point after polymerization of the gel. In some embodiments of the present disclosure, one or more compounds providing information about the status of a culture are not incorporated with a hydrogel. In some of these embodiments, the one or more compounds are used in conjunction with a hydrogel. In some embodiments, one or more compounds providing information about the status of a culture are pH-sensitive compounds. pH-sensitive compounds for use with the present disclosure may be a pH-sensitive dye, which may be of the same type commonly found in cell culture media or of a different type.

Accordingly, additional embodiments of the present disclosure feature the inclusion of one or more compounds that provide information about the status of a cell culture that are reactive to pH, temperature, ionic strength, solvent composition, pressure, electrical potential and/or the presence or absence of particular, discrete molecular species in the culture media, in a hydrogel and/or in culture cells. Compounds for use with embodiments of the present disclosure include compounds that indicate status via the absorption of electromagnetic energy and compounds that indicate status via the emission of electromagnetic energy at particular wavelengths, including fluorescent and luminescent compounds.

Non-Invasive pH Monitoring

In some embodiments of the present disclosure, one or more pH-sensitive dyes are incorporated into the hydrogel wherein the dye molecules can exist in one of two possible states, each molecular state having a particular electromagnetic absorption or emission signature (e.g., in one state, an individual dye molecule absorbs or emits electromagnetic energy at a particular discrete wavelength, whereas when the individual dye molecule is in the other state, it absorbs or emits electromagnetic energy at a different particular discrete wavelength). In some embodiments, by measuring the absorption or emittance of electromagnetic energy by molecules in the cell culture at the discrete wavelengths at which the molecules absorb or emit energy, and comparing the relative amount of absorption or emittance at different wavelengths to one another, it is possible to ascertain the relative amounts of dye molecules in each of the states. From the relative amounts of dye molecules in each state, it is possible to calculate a pH measurement for the cell culture. In some embodiments, the pH of a cell culture is visually qualified by observing the change in color or appearance of the dye. In some embodiments, a particular binary state pH-sensitive dye (i.e., one with two molecular states corresponding to two different absorption spectra) is incorporated into a hydrogel of the present disclosure. Once introduced into a cell culture via the introduction of the hydrogel to the culture, the pH-sensitive dye may remain essentially entirely associated with the hydrogel, or may be released immediately or at some point into the cell culture media so that the dye is found in the media as well as in the hydrogel, or is eventually found predominantly or essentially in the cell culture media or associated with the cultured cells. At high and low pH readings, predominately all of the dye molecules will exist in one of the two states, one state corresponding to a high pH reading, the other to a low pH reading. In some embodiments, the high and low pH readings at which all of the dye molecules exist in one state or the other are readings outside of the range of pH values compatible with continued cell growth or survival in the culture or with optimal conditions in the cell culture media.

In some embodiments, the particular pH-sensitive dye suitable for use will have a range of pH readings bounded by a lower number and an upper number, the lower representing a pH reading below which essentially all of the molecules are in one state (a protonated (acidified) form of the dye) and the upper representing a pH reading above which essentially all of the molecules are in the other state (the non-protonated (non-acidified/basic) form of the dye). In environments with pH readings between these two boundaries, the dye will exist in a mixture of the two states, with more dye molecules existing in the acidic state than the basic state in environments with a pH reading closer to the lower boundary and more dye molecules existing in the basic state than the acidic state in environments with a pH reading closer to the upper boundary. Within the range of pH readings between the boundary values, discrete ratios of acidic state molecules and basic state molecules correspond to discrete pH readings. The relative amounts of dye molecules in each of the two states can be detected, in general, by measuring the absorption of electromagnetic spectra of electromagnetic energy passing through and/or the measuring the electromagnetic spectra emanating from the culture at the two wavelengths at which the dye molecules will absorb electromagnetic energy, depending on their individual states. From the relative amounts of electromagnetic energy being absorbed by the dye molecules in a culture at two discrete frequencies, a pH reading for the culture can be calculated. In some embodiments, a change in the relative amounts of dye molecules in each of the two states is ascertained with visual inspection. In preferred embodiments, the procedure for measuring the absorbance of light by compounds in a cell culture at discrete frequencies can be done without opening and/or physically manipulating the cell culture vessel. In additional embodiments, the method for calculating a pH reading for a culture is an automated method wherein pH reading data is gathered, stored and/or transmitted for concurrent or later perusal by personnel without monitoring of the method or input from personnel.

In one embodiment, the polymer hydrogel may comprise optically active nanoparticles, e.g., fluorescent nanoparticles, quantum dots or dye-tagged nanoparticles. In some preparations, the nanoparticles are less likely to be extracted from or move around in the polymer hydrogel. In addition, the nanoparticles may be less prone to photo-bleaching. The nanoparticles may by introduced by mixing them with one of the components of the polymer hydrogel. For example, inclusion of optically active nanoparticles in the network may be accomplished by directly mixing an aqueous nanoparticle suspension into the reaction mixture. A typical sample might consists of 50 µL of nanoparticle suspension combined with 300 µL of the a precursor mixture, e.g. H-600. This mixture can be cured for 6 hours at 60° C. to produce a network with nanoparticles embedded throughout.

One type of optically active nanoparticles that may be used in the polymer hydrogel are traditional quantum dots. These include semiconductor types, such as Cds or CdSe having a ZnS or ZnSe passivation layer on the outside, as well as other materials, such as silica-based nanoparticles comprising a fluorophore (e.g., C•Spec®). The nanoparticles may be pH-sensitive, pH-insensitive, or a mixture thereof. For embodiments using some fluorescent nanoparticles, e.g. C•Spec® by Hybrid Silica Technologies, pH can be assessed via fluorescence emission. The particle may have a dye on the inside (reference) and one on the outside (sensing) wherein both are excited and the ratio of the fluorescence intensity of the sensing dye compared to that of the reference dye provides a metric to track pH.

The nanoparticles would preferably have a particle size distribution such that inclusion into the precursor mixture would not settle, but have an even distribution throughout the final polymer hydrogel. The particle size distribution may vary depending on the density and viscosity of the precursor mixture. Preferably, the settle viscosity is sufficiently low to reduce or prevent significant settling between the time the particles are added and the time the network reaches its gel point.

Monitoring Systems and Devices

Embodiments of the present disclosure include systems capable of handling a wide range of sample volumes. In some embodiments, the sensitivity of the system is tunable by careful selection of the wavelengths to be monitored, taking into considering the type(s) of dye(s) being used and the environmental conditions to be sensed. In some embodiments of the present disclosure, the system can monitor absorbance at more than two wavelengths, either to further improve the accuracy and sensitivity of the optical sensing system or to allow for independent readings of key environmental variables (pH, ion concentration, etc.) from multiple environmentally responsive dyes. In some embodiments, dye-dye quenching is utilized as a means of detecting and quantifying swelling itself, since the optical properties of many dye molecules change substantially when they are in close proximity.

Apparatus for pH Monitoring

Embodiments of the present disclosure include devices for use in monitoring the status of cell cultures. In some embodiments of the present disclosure, an apparatus for wavelength-radiometric pH measurement typically features an LED light source, a lens, an intervening cell culture, a lens, an optical filter and a photo detector, in that order or in some other arrangement. Non-invasive, pH-measuring apparatus of the present disclosure include apparatus that comprise one or more light sources and one or more devices for receiving light from one or more light sources. In some embodiments of the present disclosure, the one or more light sources may also comprise lenses, fiber optic cables and any other parts for directing, focusing or otherwise manipulating light. In some embodiments of the present disclosure, the one or more devices for receiving light from one or more sources comprise a means for measuring the amounts of various discrete wavelengths of light received by the device. The one or more devices for receiving light may also comprise lenses, fiber optic cables, optical filters and any other parts for directing, focusing, selecting or screening wavelengths of light or otherwise manipulating light.

Figure 2:
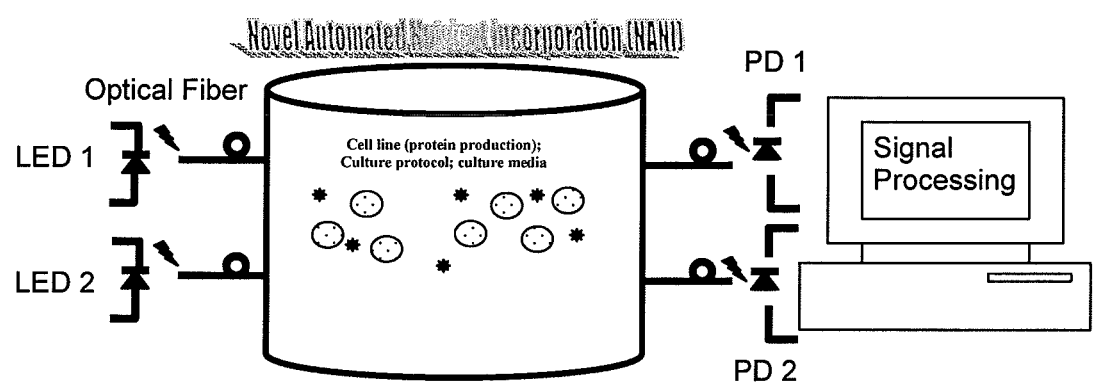
FIG. 2 shows an embodiment of the non-invasive cell culture monitoring device of the present disclosure.

In some embodiments related to pH monitoring, the system will comprise two LEDs, optical fiber, and two photodetectors, as shown in FIG. 2. The optical fiber will not be inserted into the sample solution, making this non-contact method suitable for long-term monitoring without contamination of the fiber tip or the sample. This method will also greatly reduce the amount of human intervention required to maintain viable cell cultures, and will readily allow for online monitoring. Finally, the setup may be highly cost effective, in part, due to the use of inexpensive light sources (light-emitting diodes, LEDs) and photodetectors (PD) versus what is found in commercially available UV-Vis spectrophotometers.

In preferred embodiments of the present disclosure, the apparatus feature one or more LED light sources, one or more lenses, one or more optical filters and one or more devices for receiving light comprising one or more photo detectors. In a preferred embodiment of the present disclosure, two LED sources produce light that is guided toward a cell culture by fiber optic cables. The cell culture comprises a pH-sensitive dye, the molecules of which exist in two discrete states, each with a discrete light absorption frequency. After emerging from the LED sources and being directed towards the culture, the two light beams pass through the culture, the various frequencies of light comprising the light beam possibly being absorbed, to varying degrees by wavelength, by molecules in the culture. After reemerging from the culture, the light beams are focused by lenses onto optical filters, pass through optical filters that only permit light of discrete wavelengths of interest to pass through, and enter photo detector devices that measure the intensity of light received. Each optical filter selects a different wavelength of light; the wavelengths are selected correspond to wavelengths that are absorbed by pH-sensitive dye molecules, one wavelength corresponding to one state of two possible for the molecule. Information about the amount of light received is sent to a computational device that computes a pH reading by comparing the amount of light received by the photo detectors, according to Lambert-Beer's law. In some embodiments, the pH reading is displayed on the computational device. In some embodiments, the pH reading is transmitted to another device that may record or display the reading. In a preferred embodiment, the two wavelengths selected by the optical filters are 560 nm and 425 nm. In some embodiments, air and/or cell-free media are used as reference materials to ascertain the amount of light absorbance by the culture.

Embodiments of the present disclosure use two light sources to measure absorbance at two wavelengths as compared to air or to a media standard in order to reduce or eliminate problems of light source fluctuation or environmental noise. Some embodiments of the present disclosure comprise additional parts to the apparatus, including a mechanical system for moving the optical elements from one culture to another culture, and/or to move multiple cultures to a position where the optical elements can perform the method in a sequential manner. Some embodiments feature automation of the mechanical system, allowing for hands-free assessment of pH readings in two or more cultures. Embodiments of the present disclosure include apparatus capable of real-time and/or continuous monitoring of pH in cell cultures of a variety of sizes. Persons with skill in the art would recognize that the pH readings generated by apparatus of the present disclosure could be transmitted or relayed to personnel by numerous methods, including via a computer network.

Embodiments of the present disclosure permit pH readings to be taken without physical contact between the cell culture media and the sensor device that provides data from which a pH reading can be measured or calculated. This permits pH readings to be taken without opening of cell culture vessels, which reduces the risk of cell culture contamination.

Additional embodiments of the present disclosure include apparatus with additional lenses for focusing the light beams emerging from the LED-fiber optic components onto the cell culture vessel in order to enhance the amount of light delivered from the light source to the dye; additional fiber optic devices to gather and/or direct light after light has passed through the cell culture; and large diameter optical fiber devices that confine light to a greater degree, thus increasing coupling efficiency. Additional embodiments of the present disclosure include various additional method steps, including removing (e.g., via pumping) a very small percentage of culture media through narrow diameter tubing for survey and subsequently returning the media back to the container, so as to reduce the optical path length and minimize losses while testing with the optical device. In some of these embodiments, two 45 degree angle polished optical fibers are used to transmit and receive the optical light through the tubing. In these embodiments, a simple and compact mechanism is designed for temporarily removing an amount of media from a cell culture for analysis. A variety of different media amounts may be analyzed in various embodiments and the mechanism allows for analysis of cell culture media without violating the enclosure of the cell culture container, as the interior of tube is contiguous with the cell culture container interior from the initiation of the culture. These embodiments may also permit alterations to the method by permitting measurement based on a shorter light path through the cell culture media. In some embodiments, instead of measuring the whole transmission spectrum (sensitive to environmental conditions and difficult to obtain for poorly transmitting samples), the transmitted intensity at two wavelengths is measured and their ratio is monitored as a means of environmental sensing, increasing the sensitivity of the system. In some embodiments, avalanche photodiodes (APDs) are used instead of conventional photodiodes to increase the response of the system. The responsivity (defined as the amount of electrical current produced with a given input of optical power) of a typical APD is usually on the order of 75-80 A/W, two orders of magnitude higher than that of a conventional photodiode (0.5-0.7 A/W) (responsibility being defined as the output current/input optical power).

Non-Invasive Cell Culture Monitoring Using Hydrogels

Embodiments of the present disclosure feature use of hydrogels in cell culture in conjunction with monitoring devices. In preferred embodiments, the hydrogel for use in cell culture contains a compound that reacts to changing conditions in the cell culture with changes in its absorption spectra. In particular preferred embodiments, this compound is a pH-sensitive dye. A cell culture containing a hydrogel of the present disclosure can then be monitored for changes in the condition using a non-invasive device.

EXAMPLES

Example 1

Hydrogel Formulations

Tables 1-3 list epoxy-amine based hydrogel formulations of the present disclosure. Components A and B are precursors. Component C is a linker or cross-linker.

The hydrogel polymer formulations were prepared by calculating an amount of each component(s) to achieve a 1:1 ratio of amine hydrogens to epoxy groups. The components were mixed using a Flacktek DAC-150FVZ Speed Mixer to both mix and degas the mixture. The mixture was then transferred into a mold, e.g. a multi-well plate for small beads or a rectangular tray for plaques. The mixture was cure at either room temperature or at 60° C. depending on the particular formulation. The curing time for the mixtures ranged from minutes to hours.

For example, one three-dimensional network was prepared by reacting Heloxy® modifier 48 with Jeffamine® ED-600 at a 1:1 stoichiometric ratio. A calculated amount of Heloxy®-48 was mixed with ED-600 to give a total volume of 50 mL. The reaction mixture was poured into PFA trays and thermally cured at 60° C. for 6 hours in a convection oven under vacuum pressure, resulting in uniformly cross-linked network in the form of sheets.

Any ratio of precursor components that form a pH-sensitive hydrogel, however, may be used. Likewise, any ratio of linker/crosslinker components that form a pH-sensitive hydrogel may be used. The hydrogels of the present disclosure may comprise many different arbitrary blends of precursors and or linker/crosslinkers. In Table 1, the term "f" denotes the functionality of a component for the purposes of the reaction chemistry involved.

In Table 2, swelling at pH 2 and pH 9 is provided. The percent change in swelling from pH 2 to pH 9 (i.e. delta) and the ratio of swelling at pH 2 vs. pH 9 are also provided. Swelling values in brackets "[ ]" are estimates. Swelling values can provide an indication of hydrogel pH sensitivity.

For example, a large delta value means a relatively larger increase in swelling at low pH than at high pH. While the delta value provides some indication of how much more release, e.g., of an agent, the hydrogel will have at low pH versus at high pH, the delta value does not differentiate between a hydrogel that releases very little at high pH and a hydrogel that releases a lot at high pH, provided the level of release at low pH shifts in tandem. In these cases, the delta value is the same.

Similarly, a large ratio value means a relatively larger increase in swelling at low pH as compared to high pH. While the ratio value provides some indication of how much more release, e.g., of an agent, the hydrogel will have at low pH versus at high pH, the ratio value does not differentiate between a hydrogel that releases very little at both low and high pH and a hydrogel that release a lot at both low and high pH, provided both release the same amount relative to the related low pH and high pH values. In these cases, the ratio value is the same.

In some embodiments, a hydrogel may have a large ratio value and a large delta value. In other embodiments, a hydrogel may have a small ratio value and a small delta value. In still other embodiments, a hydrogel may have a small ratio value and a large delta value. Finally, in some embodiments, a hydrogel may have a large ratio value and a small delta value. The characterization of large and small depends, in part, on the cell line being cultured and its particular needs under culture conditions. For instance, for a very metabolically active cell line that consumes glucose and produces lactic acid relatively quickly, the concern is more with providing nutrient capacity than optimizing a ratio or delta value. In this case, a hydrogel having a ratio of 1 and the delta of 0% (e.g., a pH-insensitive hydrogel in regard to agent release) might be acceptable so long as the right amount of the hydrogel is used (e.g., having the right surface to volume ratio) because enough glucose would be available within the system to maintain the cell culture, assuming the hydrogel would still be acting to neutralize the lactic acid being produced.

On the other hand, for a less metabolically active cell line that is sensitive to pH and glucose levels, a higher ratio would be preferred to prevent release of the agent until the pH were sufficiently acidic to avoid the addition of too much agent (e.g., glucose). But the delta need not be very big, since a large amount of glucose is not being released as a result of a pH drop due to the low metabolic activity of the cells.

Acid absorption capacity is also provided in Table 2. Acid absorption capacity in the wet state assumes that the hydrogel is swollen to approximately the same extent as if it were in pH 9 water and, therefore, represents the maximum acid absorption capacity. These values may be calculated in advance based on the composition of the hydrogel, and therefore may be used to design a specific hydrogel for a specific application. The optimal acid absorption capacity depends on the needs of the cells being cultured. In some embodiments, a higher acid absorption capacity value may be preferred for very metabolically active cell lines. Likewise, a lower acid absorption capacity value may be preferred for less metabolically active cell lines.

In Table 3, a minimum and maximum glucose capacity is provided. The hydrogels of the present disclosure preferably deliver enough nutrients to maintain a viable cell culture environment for cell growth. For example, if a hydrogel lacks the capacity to deliver more than a fraction of what cells consume, the cells die. These minimum and maximum glucose capacity values can be used to optimize a hydrogel for a particular cell line. The optimization is based, in part, on knowledge of that cell line's nutrient needs under a particular set of culture conditions, as well as the amount of hydrogel used in a given cell culture.

In Tables 1-3, compositions dented with one asterisk (*) show high extractable fractions, and compositions denoted with two asterisks (**) are prophetic.

Example 2

Figure 3:
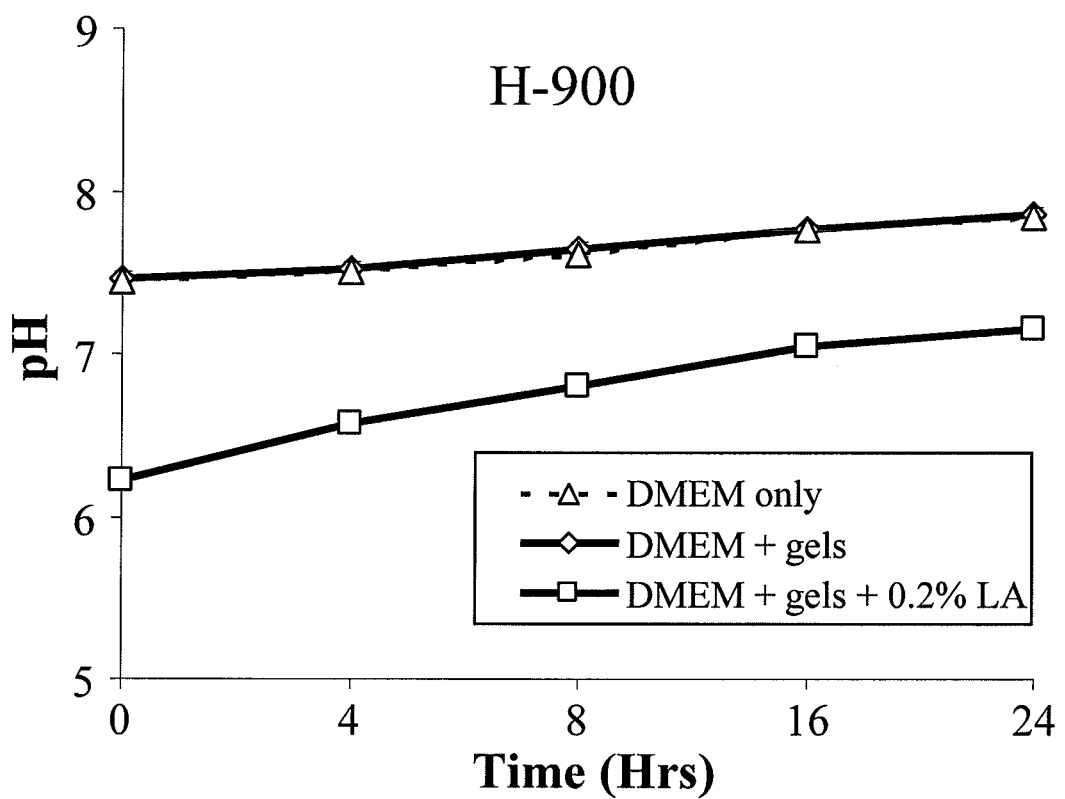
FIG. 3 shows a change in pH over 24 hours in medium with added lactic acid for one embodiment of the present disclosure.

Autoregulation of pH Changes Caused by Lactic Acid in Cell Culture Medium with Hydrogels The pH autoregulation of hydrogels of the present disclosure in Dulbecco's Modified Eagle's Medium (DMEM) was tested by the addition of 0.2% lactic acid. DMEM is a commonly used medium for culturing a wide range of different cell types. The amount of acid added was an amount sufficient to cause a reduction in pH of approximately 1 unit (e.g., 7.4 to 6.4), which is the typical pH reduction caused by 2 to 3 days of culturing a normally proliferating cell line. Changes in pH over a 24 hour period were quantified under three conditions: a) DMEM medium alone, DMEM with ~145 mg of hydrogel, and DMEM with 0.2% (weight per volume) lactic acid plus ~145 mg hydrogel. As shown in FIG. 3, addition of hydrogel formula (H-900) did not affect the pH in DMEM medium without the addition of lactic acid. However, when 0.2% lactic acid was added, which reduced the pH from ~7.4 to 6.4, the pH was raised up to 7.2 within 24 hours. This provided a change of pH over 24 hours (D24) of about 0.76±0.1. Values of D24 pH for hydrogels of the present disclosure are included in Table 4. These data demonstrate the capacity of the hydrogels to absorb lactic acid added to DMEM medium and thereby raise the pH back to physiologic levels. In Table 4, all data shown are from triplicate assays performed in parallel. Measurements denoted with an (***) were from earlier time points due to contamination or reading errors.

Example 3

Release of Glucose Loaded into Hydrogels in a pH-dependent Fashion

Figure 4:
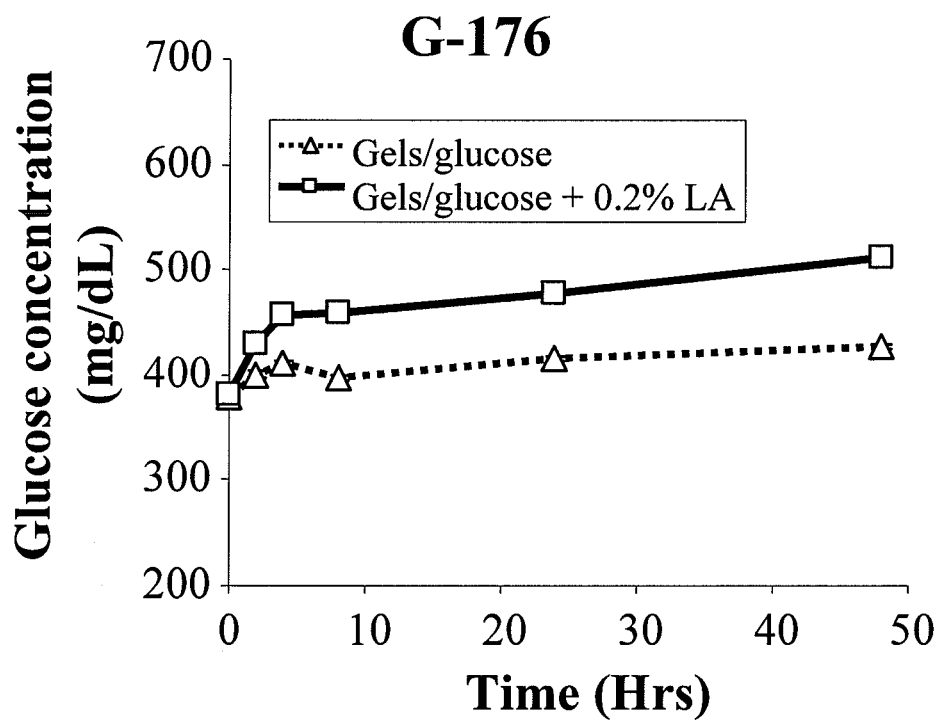
FIG. 4 shows a change in glucose released from loaded hydrogel in regular medium verses medium with added lactic acid for one embodiment of the present disclosure.

The capacity of hydrogels of the present disclosure to release glucose in DMEM medium was tested by preloading hydrogels via immersion in a 40% glucose solution and then monitoring glucose release into medium either at neutral pH or after the addition of 0.2% lactic acid. As shown in FIG. 4, glucose is released by hydrogel formula G-176 under neutral pH, but the rate and amount of glucose release was increased upon addition of lactic acid. To quantify the release of glucose for each hydrogel tested, two characteristics were determined for each condition: the slope of release over the first 8 hours in either normal medium or with added lactic acid, and the change in glucose over 24 hours (D24) in either normal medium or medium with added lactic acid; results from different hydrogel formulations are presented in Table 4. The results show that the majority of tested hydrogels exhibited an increase in slope and Δ24 when cultured in medium at a lower pH (e.g., 6.3).

Correlations between the data generated from the hydrogels of the present disclosure can be calculated as a measure of the performance of the hydrogels in cell culture media. Tables 5 and 6 list the different pH and glucose related determinations made.

Figure 5:
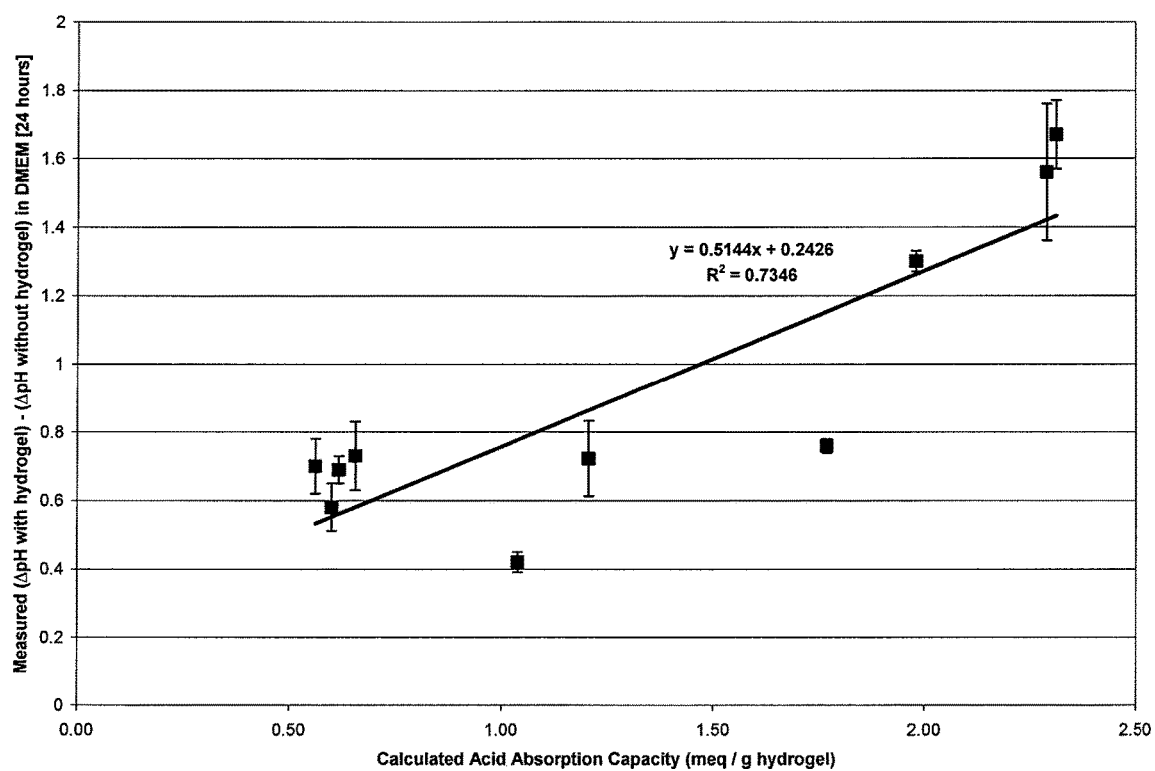
FIG. 5 shows a correlation of pH adjustment to acid absorption capacity for certain embodiments of the present disclosure.

As shown in FIG. 5, the ability of a hydrogel to adjust the pH strongly correlates to the calculated acid absorption capacity of the hydrogel. The correlation of a hydrogel to adjust the pH is also correlated to the calculated acid absorption capacity of the xerogel (e.g., dried hydrogel) ($r^2$~0.61).

Figure 6:
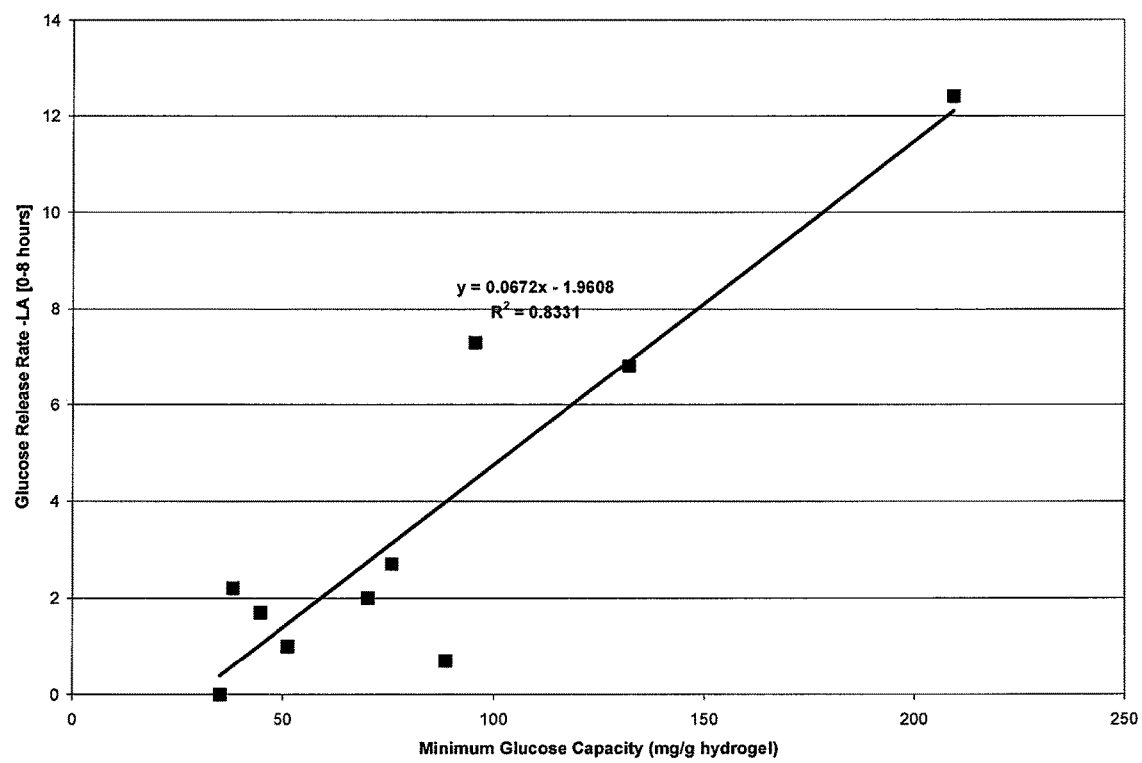
FIG. 6 shows a correlation of the minimum glucose capacity of xerogel to glucose release rate over the first 8 hours in the absence of lactic acid for certain embodiments of the present disclosure.

As shown in FIG. 6, the minimum glucose capacity of a xerogel (calculated by assuming uptake of a 40 wt % glucose solution when the material is in the high pH/low-swelling state) correlates to the glucose release rate over the first 8 hours in the absence of lactic acid. Similarly, the minimum glucose capacity of a hydrogel also correlates to the glucose release rate over the first 8 hours in the absence of lactic acid ($r^2 \sim 0.82$).

Figure 7:
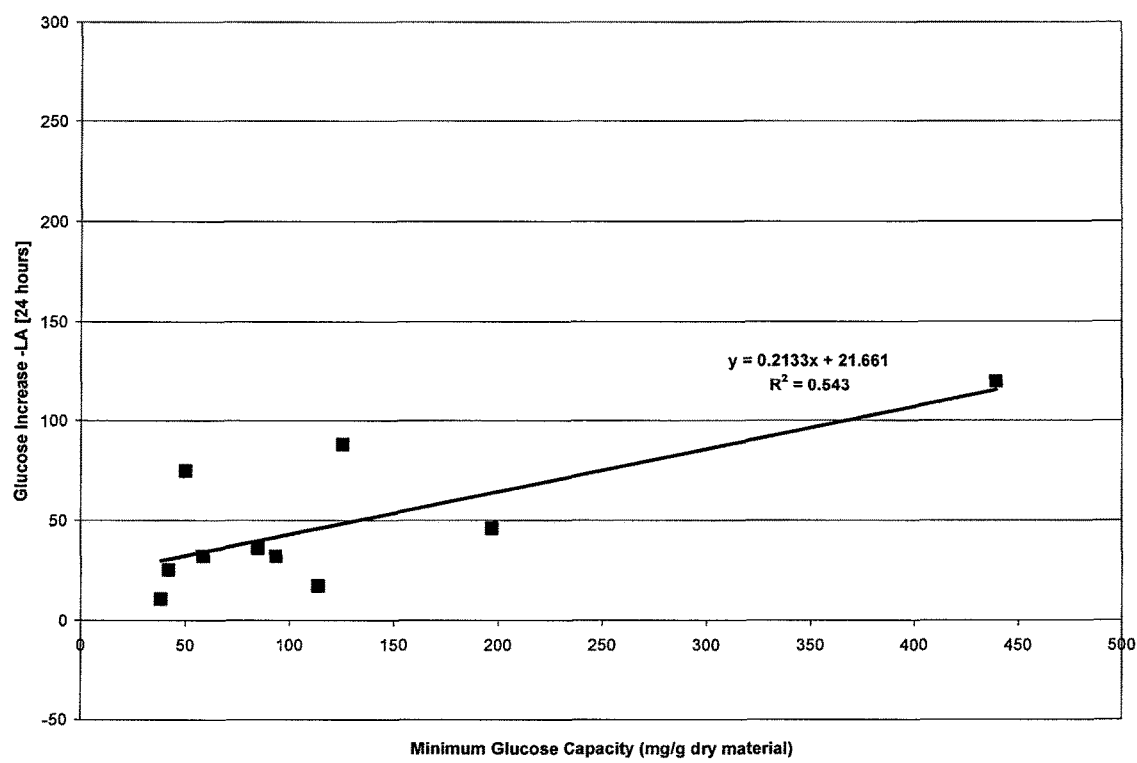
FIGS. 7 and 8 show correlations of the minimum glucose capacity of xerogel to the total glucose release over 24 hours in the absence of lactic acid for certain embodiments of the present disclosure.
Figure 8:
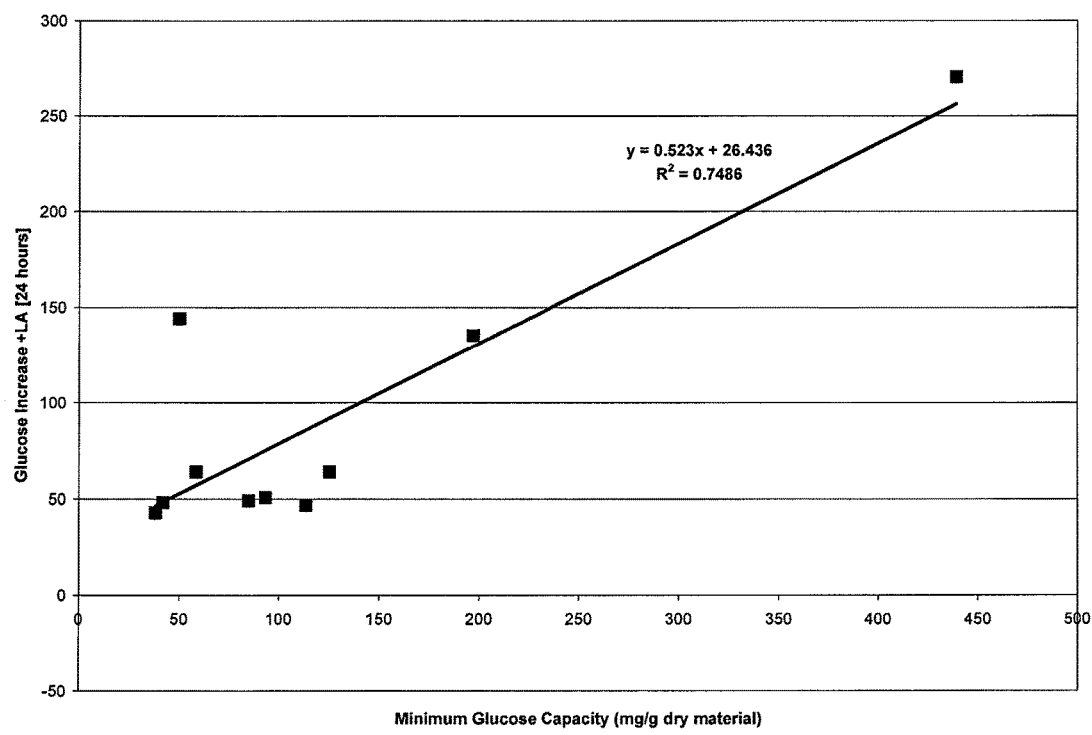
Figure 9:
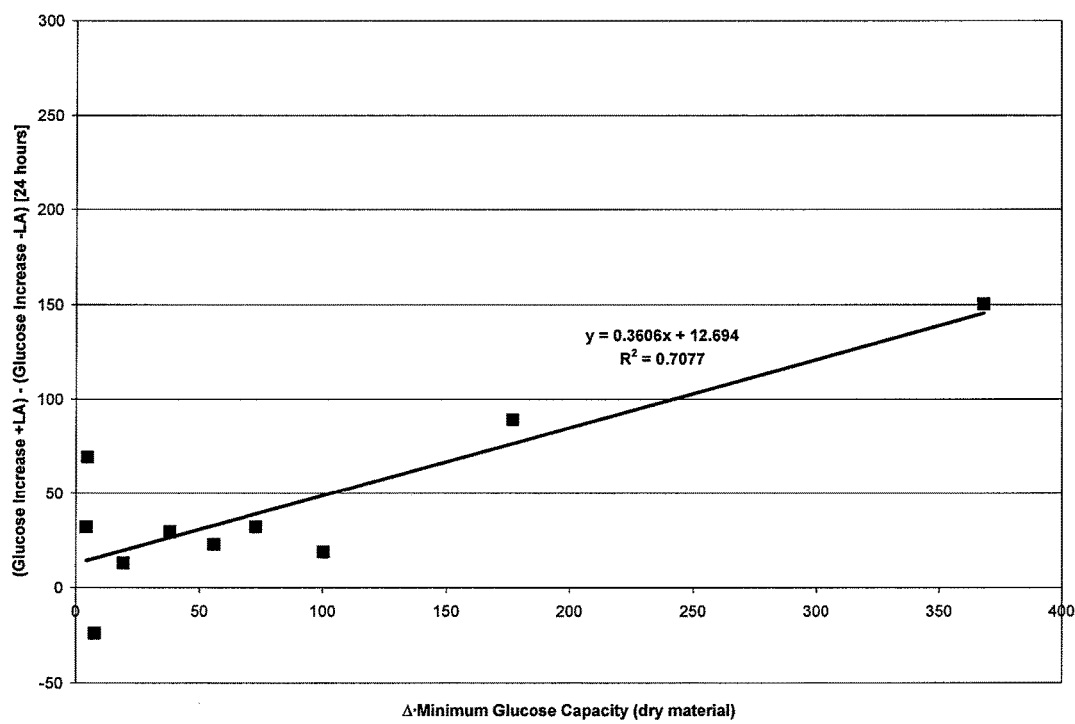
FIG. 9 shows a correlation of the product of the difference between weight percent swelling at pH 2 and at pH 9 and the minimum glucose capacity to the total glucose release over 24 hours in the absence of lactic acid for certain embodiments of the present disclosure.

As shown in FIGS. 7-9, the minimum glucose capacity of a xerogel is predictive of the total glucose release over 24 hours in the absence of lactic acid. The minimum glucose capacity of a hydrogel is also predictive the total glucose release over 24 hours in the absence of lactic acid ($r^2 \sim 0.50$). The minimum glucose capacity of a xerogel is also strongly predictive of total glucose release over 24 hours in the presence of lactic acid. The correlation of the minimum glucose capacity of a hydrogel is also correlated to the total glucose release over 24 hours in the presence of lactic acid ($r^2 \sim 0.65$).

The product of the swelling delta value and the minimum glucose capacity of a xerogel predicts the "excess" glucose released as a result of lactic acid addition. The minimum glucose capacity metric alone captures much of this data ($r^2 \sim 0.59$ and 0.49 when using minimum glucose capacity of a xerogel and the hydrogel, respectively). The product of the swelling delta value and the minimum glucose capacity of the hydrogel is also predictive. ($r^2 \sim 0.60$).

These correlations confirm that minimum glucose capacity values are more relevant to performance than maximum glucose capacity values, in part, because traditional glucose loading has always been accomplished in the absence of acid. The maximum glucose capacity values become more relevant when a hydrogel is loaded at low pH.

The present disclosure has been described herein with reference to certain examples and embodiments only. No effort has been made to exhaustively describe all possible examples and embodiments of the present disclosure. Indeed, those of skill in the art will appreciate that various additions, deletions, modifications and other changes may be made to the above-described examples and embodiments, without departing from the intended spirit and scope of the present disclosure as recited in the following claims. It is intended that all such additions, deletions, modifications and other changes be included within the scope of the following claims.

What is claimed is:

1. A composition comprising a pH-responsive hydrogel polymer and a cell culture, the pH-responsive hydrogel polymer for delivering one or more agents to a cell culture, comprising:
   (i) a pH-sensitive precursor,
   (ii) a linker, and
   (iii) one or more agents selected from the group consisting of a pH-sensitive dye, nutrient, amino acid, growth factor, a cell media pH-regulating agent, and mixtures thereof, wherein the pH-sensitive precursor and the linker are covalently attached to each other,
   wherein the pH-sensitive precursor comprises an average functionality of more than two amine hydrogens per molecule, and the linker comprises an average functionality of at least two epoxy groups per molecule, or
   the pH-sensitive precursor comprises an average functionality of at least two amine hydrogens per molecule, and the linker comprises an average functionality of more than two epoxy groups per molecule,
   wherein the dried hydrogel network exhibits swelling in an aqueous environment, wherein the degree of swelling in an aqueous environment at pH 2 is between about 10% and about 200%, the difference between the degree of swelling in an aqueous environment at pH 2 and the degree of swelling in an aqueous environment at pH 9 is between about 3% and about 190% and the ratio of the swelling in an aqueous environment at pH 2 to swelling in an aqueous environment at pH 9 is between about 1.2 and about 20.8, and
   wherein the pH-responsive hydrogel polymer is capable of delivering the one or more agents to the cell culture and the one or more agents is released into the cell culture in response to a change in the cell culture pH.

2. The composition of claim 1, wherein the pH-sensitive precursor comprises an average functionality of more than two amine hydrogens per molecule and the linker comprises an average functionality of at least two epoxy groups per molecule.

3. The composition of claim 1, wherein the pH-sensitive precursor comprises an average functionality of at least two amine hydrogens per molecule and the linker comprises an average functionality of more than two epoxy groups per molecule.

4. The composition of claim 1, wherein the pH-sensitive precursor is selected from the group consisting of amine-terminated poly(ethylene oxide), poly(propylene oxide), poly(tetramethylene oxide), poly(dimethylsiloxane), poly(ethyleneimine), and mixtures or copolymers thereof.

5. The composition of claim 1, wherein the pH-sensitive precursor is selected from the group consisting of poly(dimethyl-co-aminopropylmethylsiloxane), 1,4-bis(3-aminopropyl)piperazine, polyetheramine having an approximate molecular weight of between about 148 and about 5000 Daltons, poly(ethyleneimine) having an approximate molecular weight of between 600 and 1,800 Da, homopiperazine, 1-(2-aminoethyl)piperazine, polyetheramine and mixtures thereof.

6. The composition of claim 1, wherein the linker is selected from the group consisting of trimethylolpropane triglycidyl ether, glycerol triglycidyl ether, propoxylated glycerol triglycidyl ether, poly(glycidyl methacrylate), sorbitol hexaglycidyl ether, PEG-DGE and mixtures thereof.

7. The composition of claim 1, wherein the cell media pH-regulating agent is a buffer or alkaline species.

8. The composition of claim 1, wherein the nutrient is L-glutamine, L-glutamine in the form of a dipeptide, or glucose.

9. The composition of claim 1, wherein the change in the cell culture pH is more than about 0.10 pH units.

10. A method for delivering one or more agents to a cell, comprising the steps of: (i) adding the hydrogel polymer of claim 1 to a media comprising the cell, wherein the hydrogel polymer is capable of releasing the one or more agents into the media, and (ii) culturing the cell under conditions wherein the one or more agents is released into the media, wherein the one or more agents is delivered to the cell.

11. A method for maintaining an optimal cell culture pH, comprising the steps of: (i) adding the hydrogel polymer of claim 1 to the cell culture, wherein the one or more agents comprises a pH-regulating agent, and wherein the hydrogel polymer is capable of releasing the pH-regulating agent into the cell culture, and (ii) culturing the cell under conditions wherein the pH-regulating agent is released into the cell culture in response to a change in the pH of the cell culture, wherein an optimal cell pH is maintained.

12. The method of claim 11, wherein the optimal pH is within the range of 6.0 to 8.5 pH units.

13. A method for maintaining an optimal cell culture glucose level, comprising the steps of:
   (i) adding the hydrogel polymer of claim 1 to the cell culture, wherein the one or more agents comprises glucose, and wherein the hydrogel polymer is capable of releasing the glucose into the cell culture, and (ii) culturing the cell culture under conditions such that the glucose is released into the cell culture in response to a change in the pH of the cell culture, wherein an optimal cell culture glucose level is maintained.

14. The method of claim 13, wherein the optimal glucose level is within the range of 3.0 g/L to 5.5 g/L.

15. A method for maintaining an optimal cell culture L-glutamine level, comprising the steps of:
(i) adding the hydrogel polymer of claim 1 to the cell culture, wherein the one or more agents comprises L-glutamine and wherein the hydrogel polymer is capable of releasing the L-glutamine into the cell culture, and
(ii) culturing the cell culture under conditions such that the L-glutamine is released into the cell culture in response to a change in the pH of the cell culture, wherein an optimal cell culture L-glutamine level is maintained.

16. The method of claim 15, wherein the optimal L-glutamine level is within the range of 1.0 to 10.0 mmol.

17. The composition of claim 1, wherein the ratio of the swelling in an aqueous environment at pH 2 to swelling in an aqueous environment at pH 9 is between about 1.2 and about 2.8.

18. The composition of claim 1, wherein the pH-sensitive precursor is selected from the group consisting of amine functional polyethers, polyimines or polysiloxanes.

19. The composition of claim 1, wherein the linker is selected from the group consisting of a polyol glycidyl ether, an aliphatic polyepoxide, a cycloaliphatic polyepoxide, an aromatic polyepoxide, an alkoxylated polyol glycidyl ether and mixtures thereof.

20. The composition of claim 1, wherein the linker is a polyol glycidyl ether, wherein the polyol is selected from the group consisting of glycerol, trimethylolethane, trimethylolpropane, pentaerythritol and sorbitol.

21. The composition of claim 1, wherein the molar ratio of amine hydrogens to epoxy groups is between about 2:1 to 1:2.

22. The composition of claim 1, wherein the molar ratio of amine hydrogens to epoxy groups is about 1:1.

* * * * *